(12) United States Patent
Gouya et al.

(10) Patent No.: US 9,637,744 B2
(45) Date of Patent: May 2, 2017

(54) METHODS AND PHARMACEUTICAL COMPOSITIONS FOR THE TREATMENT OF ERYTHROPOIETIC PROTOPORPHYRIA

(71) Applicants: INSERM (INSTITUT NATIONAL DE LA SANTE ET DE LA RECHERCHE MEDICALE), Paris (FR); UNIVERSITE PARIS DIDEROT—PARIS 7, Paris (FR); UNIVERSITE DE VERSAILLES SAINT-QUENTIN-EN-YVELINES, Versailles (FR); ASSISTANCE PUBLIQUE-HOPITAUX DE PARIS (APHP), Paris (FR)

(72) Inventors: Laurent Gouya, Paris (FR); Jean-Charles Deybach, Paris (FR); Herve Puy, Paris (FR); Vincent Oustric, Paris (FR)

(73) Assignees: INSERM (INSTITUT NATIONAL DE LA SANTE ET DE LA RECHERCHE MEDICALE), Paris (FR); UNIVERSITE PARIS DIDEROT—PARIS 7, Paris (FR); UNIVERSITE DE VERSAILLES SAINT-QUENTIN-EN-YVELINES, Versailles (FR); ASSISTANCE PUBLIQUE-HOPITAUX DE PARIS (APHP), Paris (FR)

( * ) Notice: Subject to any disclaimer, the term of this patent is extended or adjusted under 35 U.S.C. 154(b) by 0 days.

(21) Appl. No.: 14/897,698

(22) PCT Filed: Jun. 13, 2014

(86) PCT No.: PCT/EP2014/062369
§ 371 (c)(1),
(2) Date: Dec. 11, 2015

(87) PCT Pub. No.: WO2014/198890
PCT Pub. Date: Dec. 18, 2014

(65) Prior Publication Data
US 2016/0122767 A1 May 5, 2016

(30) Foreign Application Priority Data
Jun. 13, 2013 (EP) .................................... 13305796

(51) Int. Cl.
*C12N 15/11* (2006.01)
*C07H 21/04* (2006.01)
*C12N 15/113* (2010.01)

(52) U.S. Cl.
CPC ...... *C12N 15/1137* (2013.01); *C12N 2310/11* (2013.01); *C12N 2310/3231* (2013.01); *C12N 2310/3233* (2013.01); *C12N 2320/33* (2013.01); *C12N 2320/34* (2013.01); *C12Y 499/01001* (2013.01)

(58) Field of Classification Search
CPC . C12N 15/111; C12N 15/113; C12N 2310/11; C12N 2310/113; C12N 2320/30; C12N 2320/33
See application file for complete search history.

(56) References Cited

U.S. PATENT DOCUMENTS

| | | | | |
|---|---|---|---|---|
| 2010/0015051 | A1* | 1/2010 | Labhasetwar | A61K 9/5153 424/1.69 |
| 2014/0336238 | A1* | 11/2014 | Collin | C12N 15/113 514/44 A |

FOREIGN PATENT DOCUMENTS

WO    2008/025094 A1    3/2008

OTHER PUBLICATIONS

Gouya et al., The penetrance of dominant erythropoietic protoporphyria is modulated by expression of wildtype FECH, 2002, Nature Genetics, vol. 30, pp. 27-28.*
Aartsma-Rus et al., Exonic sequences provide better targets for antisense oligonucleotides than splice site sequences in the modulation of Duchenne Muscular Dystrophy splicing, 2010, Oligonucleotides, vol. 20, pp. 69-77.*
Oustric, V., "Therapie genique appliquee a la protoporphyrie erythropoietique: correction d'un epissage alternatif anormal", Universite De Versailles Saint-Quentin-En-Yvelines, Oct. 25, 2012, Web, Only English language abstract considered.
Havens et al., "Targeting RNA splicing for disease therapy", Wiley Interdisciplinary Reviews: RNA, Mar. 19, 2013, pp. 247-266, vol. 4, No. 3.
Hammond et al., "Genetic therapies for RNA mis-splicing diseases", Trends in Genetics, Apr. 15, 2011, pp. 196-205, vol. 27, No. 5.

(Continued)

*Primary Examiner* — Dana Shin
(74) *Attorney, Agent, or Firm* — Whitham, Curtis & Cook, P.C.

(57) ABSTRACT

The present invention relates to methods and pharmaceutical compositions for the treatment of Erythropoietic Protoporphyria. In particular, the present invention relates to a method for increasing the amount of functional FECH in a erythroid cell carrying the hypomorphic allele IVS3 48C/T (rs2272783) in trans to a deleterious mutation in the FECH gene comprising the step of consisting of bringing the erythroid cell into contact with at least one antisense oligonucleotide (ASO) comprising the sequence as set forth by SEQ ID NO: 2 (5' gcagcctgagaaatgtttt 3') to prevent splicing of the cryptic exon inserted into the mutant IVS3 48C/T (rs2272783) FECH mRNA.

9 Claims, 9 Drawing Sheets

(56) References Cited

OTHER PUBLICATIONS

Figure 1A:
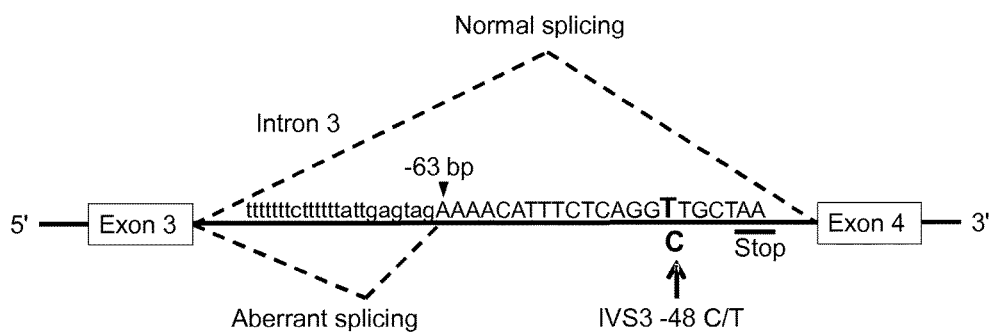

Bauman et al., "Therapeutic Potential of Splice-Switching Oligonucleotides", Oligonucleotides, Jan. 6, 2009, vol. 19, No. 1.

Schmitt et al., "La protoporphyrie erythropoietique: une maladie, deux genes et trois mecanismes moleculaires", Pathologie Et Biologie, Sep. 20, 2010, pp. 372-380, vol. 58, No. 5, L'Expansion Scientifique Francaise, Paris, FR, Only English language abstract considered.

Fu et al., "AG-dependent 3'-splice sites are predisposed to aberrant splicing due to a mutation at the first nucleotide of an exon", Nucleic Acids Research, Feb. 2, 2011, pp. 4396-4404, vol. 39, No. 10.

Kansky et al., "Erythropoietic protoporphyria: A short review", Acta Dermatoven APA, Mar. 2004, pp. 13-19, vol. 13.

Gouya et al., "Contribution of a Common Single-Nuceotide Polymorphism to the Genetic Predisposition for Erythropoietic Protoporphyria", The American Journal of Human Genetics, Nov. 15, 2005, pp. 2-14, vol. 78, No. 1.

Oustric et al., "Antisense Oligonucleotide-Based Therapy in Human Erythropoietic Protoporphyria", The American Journal of Human Genetics, Mar. 27, 2014, pp. 611-617, vol. 94, No. 4.

Kansky et al. "Erythropoietic protoporphyria", Orphanet Journal of Rare Diseases, Sep. 10, 2009, p. 19, vol. 4, No. 1, Biomed Central Ltd, LO.

Oustric, V., "Therapie genique appliquee a la protoporphyrie erythropoietique humaine: Correction d'un epissage alternatif anormal par l'utilisation d'oligonucleotides en antisens", These De Doctorat De L'Universite De Versailles-Saint-Quentin-En-Yvelines, Oct. 2012, pp. 1-204. English Translation.

* cited by examiner

Figure 7A
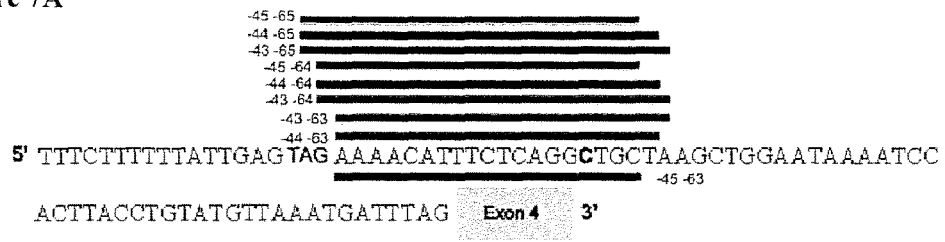
Figure 7B
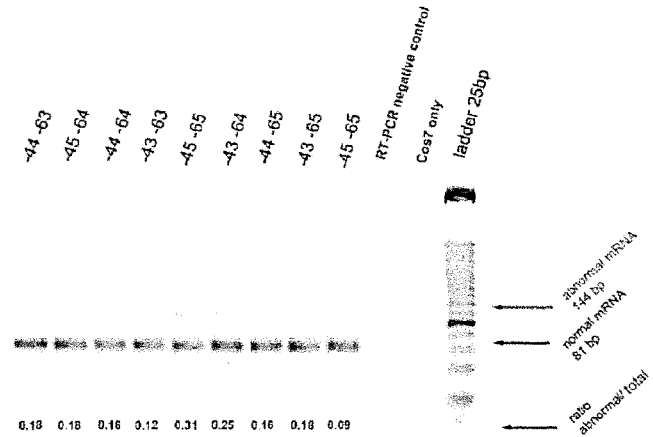
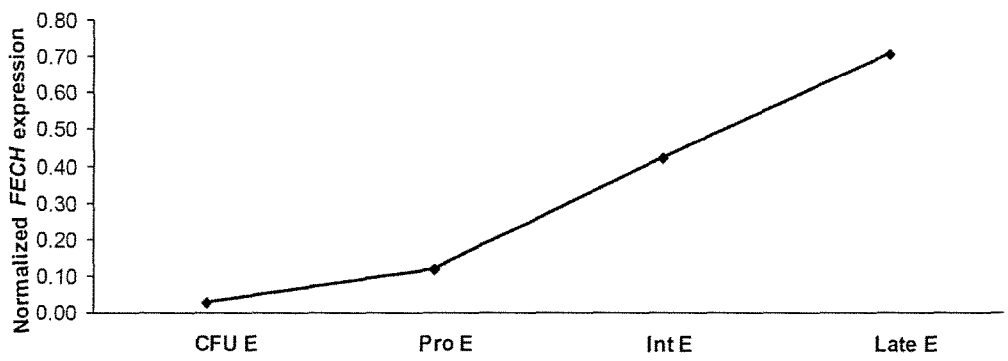
Figure 8

METHODS AND PHARMACEUTICAL COMPOSITIONS FOR THE TREATMENT OF ERYTHROPOIETIC PROTOPORPHYRIA

FIELD OF THE INVENTION

The present invention relates to methods and pharmaceutical compositions for the treatment of Erythropoietic Protoporphyria.

BACKGROUND OF THE INVENTION

Erythropoietic Protoporphyria (EPP, MIM 177000) is a rare inherited disorder caused by the partial mitochondrial deficiency of ferrochelatase (FECH, EC 4.99.1.1.), the last enzyme in the heme biosynthesis pathway (Puy et al. 2010) (Balwani et al. 1993). FECH is an inner mitochondrial membrane enzyme that catalyzes the insertion of the ferrous iron into free protoporphyrin IX (PPIX) to form heme. FECH deficiency in bone marrow erythroid cells leads to the overproduction and accumulation of PPIX in the erythrocytes, and then to secondary accumulation of PPIX in the plasma, skin, bile and feces (Puy et al. 2010). The commonest clinical manifestation is lifelong acute photosensitivity of sun-exposed skin, first appearing in early childhood. Although it is generally a benign disease, hepatic complications such as cholelithiasis or, in about 2% of cases, cirrhosis with rapidly fatal liver disease, may occur (Bloomer et al. 1998; Meerman 2000; Lyoumi et al. 2011). Cases of EPP have been reported in Europe, USA, China and Japan. So far, no case of EPP has been reported in Black African subjects. Previously it was showed that the clinical outcome of EPP is due to the inheritance of a common hypomorphic allele in trans to a deleterious mutation; this reduces FECH activity below a critical 35% threshold of enzyme activity (Gouya et al. 1996; Gouya et al. 1999). A common intronic Single Nucleotide Polymorphism (SNP), IVS3-48C/T (rs2272783), is responsible for the low-expression of the hypomorphic IVS3-48C allele by modulating the use of a 3' constitutive cryptic acceptor splice site located at the intron 3-exon 4 boundary, which leads to the pseudoexon inclusion of a portion of intron 3 (60% inclusion with the IVS3-48 C allele versus 20% with the T allele). The aberrantly-spliced mRNA includes a premature stop codon, and is degraded by a nonsense-mediated mRNA decay mechanism (NMD) (Gouya et al. 2002). In overt cases, this low, steady-state mRNA level of the hypomorphic allele also results in FECH enzyme deficiency. The overall FECH activity falls below a critical threshold of about 35% of normal, below which PPIX accumulation and photosensitivity occur (Gouya et al. 2006; Tahara et al. 2010). Several studies in USA, Europe, and Asia have confirmed that this mechanism is generally operative in EPP (Risheg et al. 2003; Wiman et al. 2003; Saruwatari et al. 2006; Kong et al. 2008; Whatley et al. 2010; Balwani et al. 2013). In France more than 90% of EPP patients show this striking inheritance pattern. Taken together, these findings suggest that therapeutic benefits in EPP patients might be achieved by even a modest increase in wild-type (WT) FECH protein. Thus, correcting this single splicing mutation represents an attractive strategy that could improve the condition of the vast majority of EPP patients. Antisense oligonucleotides (ASOs), which are generally used to inhibit gene expression, can also be used to modulate pre-mRNA splicing by targeting splice sites, or positive or negative elements that affect splice-site selection (Kole et al. 2012).

SUMMARY OF THE INVENTION

The present invention relates to methods and pharmaceutical compositions for the treatment of Erythropoietic Protoporphyria.

DETAILED DESCRIPTION OF THE INVENTION

In 90% of erythropoietic protoporphyria (EPP) patients, the disease results from the inheritance of a common hypomorphic FECH allele in trans to a deleterious FECH mutation. The activity of the resulting FECH enzyme falls below the critical threshold of 35% leading to the accumulation of free portoporphyrin IX (PPIX) in bone marrow erythroblasts and in red cells. The mechanism of low expression involves a biallelic polymorphism (IVS3-48C/T) localized in intron 3. The IVS3-48C allele increases usage of the exon 3-4 3' cryptic splice site, resulting in the transcription of an unstable mRNA with a premature STOP codon, reducing the abundance of wild-type FECH mRNA and finally reducing FECH activity. Through a candidate sequence approach and an antisense oligonucleotide-tiling method, the inventors identified a sequence which when targeted by an antisense oligonucleotide (ASO-V1) prevented usage of the cryptic splice site. In lymphoblastoid cell lines derived from symptomatic EPP patients, transfection of ASO-V1 reduced the usage of the cryptic splice site, and efficiently redirected the splicing of intron 3 towards the physiological acceptor site, thereby increasing the amount of functional FECH mRNA. Finally, the administration of ASO-V1 into human developing erythroblasts from an overtly EPP patient markedly increased the production of WT FECH mRNA, and reduced the accumulation of PPIX to a level similar to that measured in asymptomatic EPP patients. Thus, EPP appears to be a prototypic Mendelian disease where the in-vivo correction of a single splicing defect is likely to improve the condition of the vast majority of overtly EPP patients worldwide. The invention thus provides use of such exon-skipping strategy for the treatment of Erythropoietic Protoporphyria.

The present invention relates to a method for increasing the amount of functional FECH in a erythroid cell carrying the hypomorphic allele IVS3 48C/T (rs2272783) in trans to a deleterious mutation in the FECH gene comprising the step of consisting of bringing the erythroid cell into contact with at least one antisense oligonucleotide (ASO) comprising the sequence as set forth by SEQ ID NO: 2 (5' gcagcctgagaaatgtttt 3') to prevent splicing of the cryptic exon inserted into the mutant IVS3 48C/T (rs2272783) FECH mRNA.

The term "FECH" has its general meaning in the art and refers to the ferrochelatase (FECH, EC 4.99.1.1.), which is the last enzyme in the heme biosynthesis pathway (Puy et al. 2010) (Balwani et al. 1993). FECH is an inner mitochondrial membrane enzyme that catalyzes the insertion of the ferrous iron into free protoporphyrin IX (PPIX) to form heme. An exemplary native human nucleotide sequence encoding for FECH is provided in GenBank with the access number NM_000140.3 (SEQ ID NO:1).

As used the expression "deleterious mutation in the FECH gene" refers to any mutation which results in to a dysfunction of the FECH protein leading to the loss of its activity. Deleterious mutations in the FECH gene have fully been exemplified in the prior art and thus the skilled man in the art can easily such a mutation (www.hgmd.cf.ac.uk/ac/ index.php and www.ncbi.nlm.nih.gov.gate2.inist.fr/books/NBK100826/#epp-ar.molgen-.TA).

ASOs employed in the practice of the invention are generally from about 19 to about 30 nucleotides in length, and may be for example, about 19, or about 20, about 25 or about 30 nucleotides or more in length.

In a particular embodiment, the ASO comprises or consists of a nucleic acid sequence selected from Table A.

TABLE A

| position | sequence | |
|---|---|---|
| -43 -63 | tagcagcctgagaaatgtttt | SEQ ID NO: 3 |
| -44 -63 | agcagcctgagaaatgtttt | SEQ ID NO: 4 |
| -45 -63 | gcagcctgagaaatgtttt | SEQ ID NO: 2 |
| -43 -64 | tagcagcctgagaaatgttttct | SEQ ID NO: 5 |
| -45 -64 | gcagcctgagaaatgttttc | SEQ ID NO: 6 |
| -44 -64 | agcagcctgagaaatgttttc | SEQ ID NO: 7 |
| -43 -65 | agcagcctgagaaatgttttct | SEQ ID NO: 8 |
| -44 -65 | agcagcctgagaaatgttttc | SEQ ID NO: 9 |
| -45 -65 | gcagcctgagaaatgttttct | SEQ ID NO: 10 |

The ASO used in the practice of the invention may be of any suitable type. The one skilled in the art can easily provide some modifications that will improve the clinical efficacy of the ASO (C. Frank Bennett and Eric E. Swayze, RNA Targeting Therapeutics: Molecular Mechanisms of Antisense Oligonucleotides as a Therapeutic Platform Annu Rev. Pharmacol. Toxicol. 2010.50:259-293.). Typically, chemical modifications include backbone modifications, heterocycle modifications, sugar modifications, and conjugations strategies. For example the ASO may be selected from the group consisting of oligodeoxyribonucleotides, oligoribonucleotides, LNA, oligonucleotide, morpholinos, tricyclo-DNA-antisense oligonucleotides, U7- or U1-mediated ASOs or conjugate products thereof such as peptide-conjugated or nanoparticle-complexed ASOs. Indeed, for use in vivo, the ASO may be stabilized. A "stabilized" ASO refers to an ASO that is relatively resistant to in vivo degradation (e.g. via an exo- or endo-nuclease). Stabilization can be a function of length or secondary structure. In particular, ASO stabilization can be accomplished via phosphate backbone modifications.

In a particular embodiment, the ASO according to the invention is a LNA oligonucleotide. As used herein, the term "LNA" (Locked Nucleic Acid) (or "LNA oligonucleotide") refers to an oligonucleotide containing one or more bicyclic, tricyclic or polycyclic nucleoside analogues also referred to as LNA nucleotides and LNA analogue nucleotides. LNA oligonucleotides, LNA nucleotides and LNA analogue nucleotides are generally described in International Publication No. WO 99/14226 and subsequent applications; International Publication Nos. WO 00/56746, WO 00/56748, WO 00/66604, WO 01/25248, WO 02/28875, WO 02/094250, WO 03/006475; U.S. Pat. Nos. 6,043,060, 6,268,490, 6,770,748, 6,639,051, and U.S. Publication Nos. 2002/0125241, 2003/0105309, 2003/0125241, 2002/0147332, 2004/0244840 and 2005/0203042, all of which are incorporated herein by reference. LNA oligonucleotides and LNA analogue oligonucleotides are commercially available from, for example, Proligo LLC, 6200 Lookout Road, Boulder, Colo. 80301 USA. In a particular embodiment, the ASO comprise the 5' gcEgcLtgEgaEatPttZt 3'sequence as described in Table 1.

Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the ASO also include "Morpholinos" (phosphorodiamidate morpholino oligomers, PMOs), 2'-O-Met oligomers, tricyclo (tc)-DNAs, U7 short nuclear (sn) RNAs, or tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference).

Other forms of ASOs that may be used to this effect are ASO sequences coupled to small nuclear RNA molecules such as U1 or U7 in combination with a viral transfer method based on, but not limited to, lentivirus or adeno-associated virus (Denti, M A, et al, 2008; Goyenvalle, A, et al, 2004).

For use in the instant invention, the ASOs of the invention can be synthesized de novo using any of a number of procedures well known in the art. For example, the b-cyanoethyl phosphoramidite method (Beaucage et al., 1981); nucleoside H-phosphonate method (Garegg et al., 1986; Froehler et al., 1986, Garegg et al., 1986, Gaffney et al., 1988). These chemistries can be performed by a variety of automated nucleic acid synthesizers available in the market. These nucleic acids may be referred to as synthetic nucleic acids. Alternatively, ASO can be produced on a large scale in plasmids (see Sambrook, et al., 1989). ASO can be prepared from existing nucleic acid sequences using known techniques, such as those employing restriction enzymes, exonucleases or endonucleases. ASO prepared in this manner may be referred to as isolated nucleic acids.

In a particular embodiment, two or even more ASOs can also be used at the same time; this may be particularly interesting when the ASO are vectorized within an expression cassette (as for example by U7 or U1 cassettes).

In a particular embodiment, the ASO of the present invention is conjugated to a second molecule. Typically said second molecule is selected from the group consisting of aptamers, antibodies or polypeptides. For example, the ASO of the present invention may be conjugated to a cell penetrating peptide. Cell penetrating peptides are well known in the art and include for example the TAT peptide. In a particular embodiment, the second molecule is able to target the erythroid cell. In a particular embodiment, the molecule targets the transferrin receptor 1 (i.e. CD71). Several peptides and aptamers that bind with high affinity to human CD71 and display endocytotic properties are described in Lee J H, Engler J A, Collawn J F, Moore B A (2001) Receptor mediated uptake of peptides that bind the human transferrin receptor. Eur J Biochem 268:2004-2012 and in Wilner S E, Wengerter B, Maier K, de Lourdes Borba Magalhaes M, Del Amo D S, Pai S, Opazo F, Rizzoli S O, Yan A, Levy M (2012) An RNA alternative to human transferrin: a new tool for targeting human cells. Mol Ther Nucleic Acids 1:e21.

The method of the invention is particularly suitable for the treatment of Erythropoietic Protoporphyria in a patient harbouring the common hypomorphic allele IVS3 48C/T (rs2272783) in trans to a deleterious mutation in the FECH gene. Accordingly, the present invention relates to an ASO as described above for use in the treatment of Erythropoietic Protoporphyria.

In a particular embodiment; antisense oligonucleotides of the invention may be delivered in vivo alone or in association with a vector. In its broadest sense, a "vector" is any vehicle capable of facilitating the transfer of the antisense oligonucleotide of the invention to the cells. Preferably, the vector transports the nucleic acid to cells with reduced degradation relative to the extent of degradation that would result in the absence of the vector. In general, the vectors useful in the invention include, but are not limited to, naked plasmids, non viral delivery systems (electroporation, sonoporation, cationic transfection agents, liposomes, etc. . . . ), phagemids, viruses, other vehicles derived from viral or bacterial sources that have been manipulated by the insertion or incorporation of the antisense oligonucleotide nucleic acid sequences. Viral vectors are a preferred type of vector and include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art. In a preferred embodiment, the antisense oligonucleotide nucleic acid sequence is under the control of a heterologous regulatory region, e.g., a heterologous promoter. The promoter can also be, e.g., a viral promoter, such as CMV promoter or any synthetic promoters.

The present invention also provides a pharmaceutical composition containing an antisense oligonucleotide of the invention (or a vector of the invention) for the treatment of Erythropoietic Protoporphyria in a patient harbouring the common hypomorphic allele IVS3 48C/T (rs2272783) in trans to a deleterious mutation in the FECH gene.

Typically, pharmaceutical compositions of the present invention include a pharmaceutically or physiologically acceptable carrier such as saline, sodium phosphate, etc. The compositions will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, celluose, water syrup, methyl cellulose, methyl and propylhydroxybenzoates, mineral oil, etc. The formulations can also include lubricating agents, wetting agents, emulsifying agents, preservatives, buffering agents, etc. Those of skill in the art will also recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

One skilled in the art will recognize that the amount of an ASO to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.). If a viral-based delivery of ASOs is chosen, suitable doses will depend on different factors such as the viral strain that is employed, the route of delivery (intramuscular, intravenous, intra-arterial or other). Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the ASOs of the invention will likely be administered on multiple occasions, that may be, depending on the results obtained, several days apart, several weeks apart, or several months apart, or even several years apart. This is especially true where the treatment of Erythropoietic Protoporphyria is concerned since the disease is not cured by this treatment, i.e. the gene that encodes the protein will still be defective and the encoded protein will still possess an unwanted, destabilizing feature such as an exposed proteolytic recognition site, unless the ASOs of the invention are administered.

The invention will be further illustrated by the following figures and examples. However, these examples and figures should not be interpreted in any way as limiting the scope of the present invention.

FIGURES

Figure 1B:
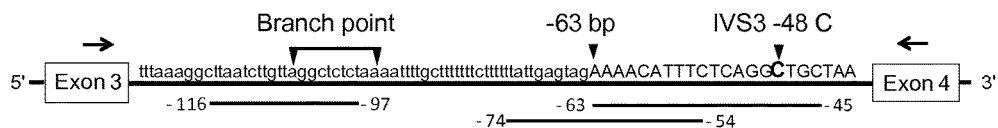
Figure 1C:
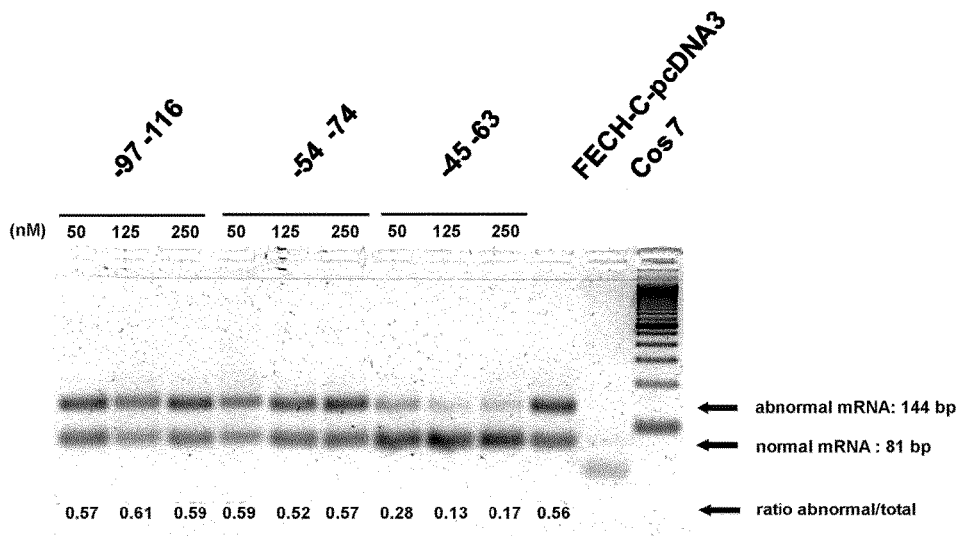

FIG. 1A-C: Schematic representation of exon 3-4 FECH gene splicing.

A: The IVS3-48T/C transition modulates the splicing efficiency of a constitutive cryptic acceptor splice site (SEQ ID NO: 58). −63 bp: position of the cryptic acceptor splice site.

B: Position of the LNA-ASOs targeting the putative cryptic branch point (−97–116), the cryptic acceptor splice site (−54–74), and both the cryptic acceptor splice site and the IVS3-48 locus (−45–63) (SEQ ID NO: 59).

⊤⊤ Putative cryptic branch point.

C: Inhibition of abnormal FECH splicing by 3 LNAs-ASO.

Cos 7 cells were transiently cotransfected with the FECH-C-pcDNA3 minigene and 50, 125, or 250 nM of the appropriate LNA oligonucleotides (Eurogentec, Angers, France) using lipofectamine 2000 reagent (Life technologies, Saint-Aubin, France). RNA was extracted 24 h after transfection with RNA plus reagent (MP Biomedical, Illkirch, France). RT PCR products are analyzed on 3% agarose gel. The migration positions of the normal exon 3-4 81-bp amplimer and the aberrantly-spliced 144-bp product are indicated on the right. PCR primers were selected to be human specific. Ratios of the aberrantly-spliced RNA to the total RNA are indicated at the bottom.

FIG. 2A-D: Restoration of WT FECH mRNA production in the LBCLs of EPP patients.

A: Pedigree of the EPP family used. "M": c. 709delT FECH gene mutation. "T": IVS3-48T allele. "C": IVS3-48C allele. Subjects I1 and II3 are asymptomatic carriers of the c. 709delT mutation. Subjects II1 and II2 are overt EPP patients. FC: FECH activity in nmoles of Zn-Mesoporphyrin/mg of protein/hour.

B: The LBCLs were transfected with 125 nM of −45–63 or mock (−43–65 sense sequence) LNA-ASOs and emetin was added 24 hours later. Total RNA was extracted 48 h after transfection. The migration positions of the normal exon 3-4

126-bp amplimer, and of the aberrantly spliced 192-bp product are indicated on the right. This represents one example of 6 experiments.

C: The ratios of the aberrantly-spliced RNA to the total RNA are presented as box plots showing the median, the quartiles, the 90th and the 10th percentiles. n=6 experiments. The Mann-Whitney statistical test was used with Prism 4 software (GraphPad software, La Jolla, USA).

D: Total RNA was extracted 24 h and 48 h after transfection with the −45−63 or mock LNA-ASOs without emetin. WT FECH RNA was analyzed by RT-qPCR with specific primers of the normal exon 3-4 spliced RNA and normalized with two genes (B2M and HPRT1). n=6 independent experiments. The Mann-Whitney statistical test was used with Prism 4 software.

Figure 3A:
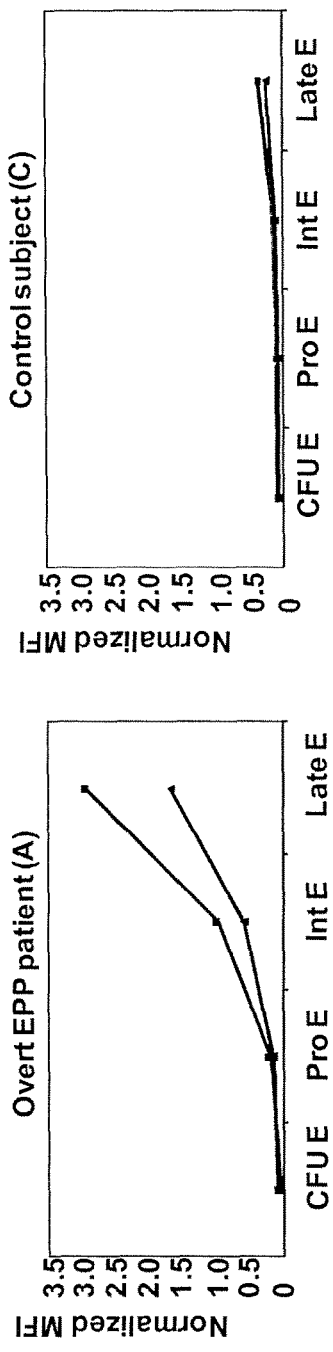

FIG. 3A and B: In-vitro erythroid differentiation of $CD34^+$ cells isolated from peripheral whole blood in the presence of 45-µM, FITC-labeled V1 or mock morpholinos.

Total mononuclear cells were isolated by Ficoll density-gradient centrifugation (LSM; PAA laboratories, Velizy-Villacoublay, France), from 60 ml peripheral whole blood. $CD34^+$ cells were purified using immunomagnetic beads (MACS CD34 MicroBead Kit; Miltenyi Biotec, Paris, France). For the erythroid differentiation, $CD34^+$ cells were grown in Iscove modified Dulbecco medium (Invitrogen, Saint Aubin, France) supplemented with 15% BIT 9500 (StemCell Technologies, Grenoble, France), 2 IU/mL EPO, 100 ng/mL SCF, 10 ng/mL IL-6 and 10 ng/mL IL-3 (Miltenyi Biotec).

Time kinetic analysis of PPIX accumulation was determined by flow cytometry at four stages of differentiation—CFU E, Pro E, Int E, and Late E. Indicated values in the graphs represent ratios between the Mean Fluorescence Intensity (MFI) values of accumulated PPIX and MFI of FITC-positive cells. (A) Normalized MFI of PPIX in erythroid cells from overt EPP patient A and control patient C, treated either with PMO-V1 (▲) or with PMO-mock (■). (B) Normalized MFI of PPIX in erythroid cells from overt EPP patient B, and asymptomatic carrier D, treated either with PMO-V1 (▲) or with PMO-mock (■).

Figure 4:
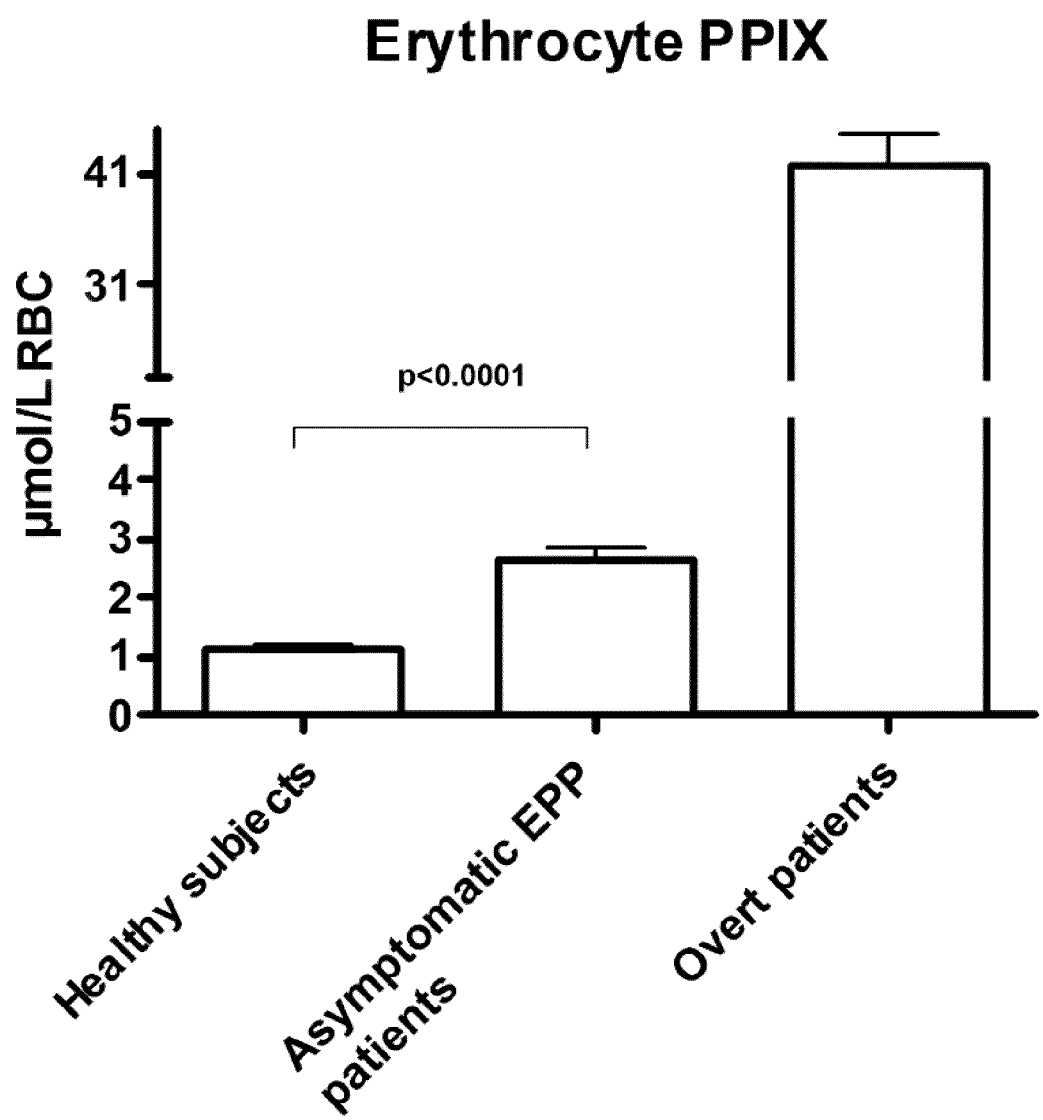

FIG. 4: Erythrocyte protoporphyrin IX in 40 EPP families.

Total erythrocyte PPIX was measured in 40 EPP families each having one overt patient, one asymptomatic patient, and one healthy subject. The results were expressed as a histogram showing the mean and the standard deviation. Means were compared using "t" test with Prism 4 software.

Figure 5A:
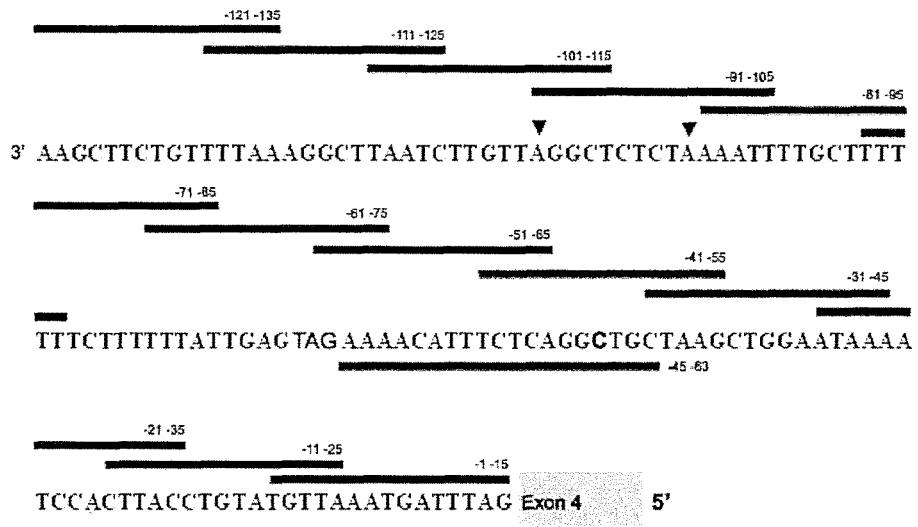
Figure 5B:
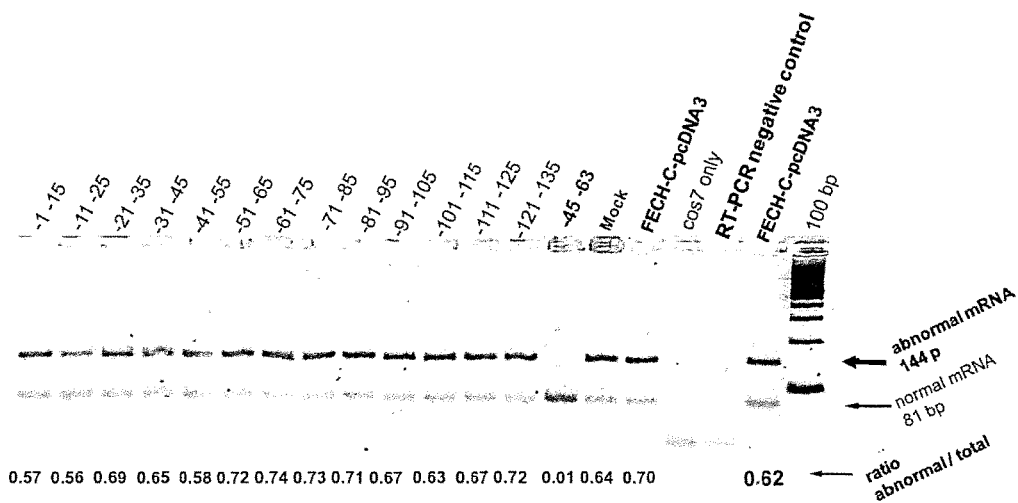

FIG. 5A and B: ASO-tiling approach to search for regulating cis-acting elements of exon 3-4 splicing residing within the 130-bp stretch upstream of exon 4.

A: Schematic representation of the binding site of the 13 ASOs used (SEQ ID NO: 60).

B: Cos 7 cells were transiently cotransfected with the FECH-C-pcDNA3 minigene and 50, 125, or 250 nM of the appropriate LNA-ASO using lipofectamine 2000 reagent. Total RNA was extracted 24 h after transfection. RT-PCR products were analyzed on 3% agarose gel. The migration positions of the normal exon 3-4 81-bp amplimer, and the aberrantly-spliced 144-bp product are indicated on the right. PCR primers had been chosen to be human specific. Ratios of the aberrantly-spliced RNA to the total RNA are indicated at the bottom.

Figure 6A:
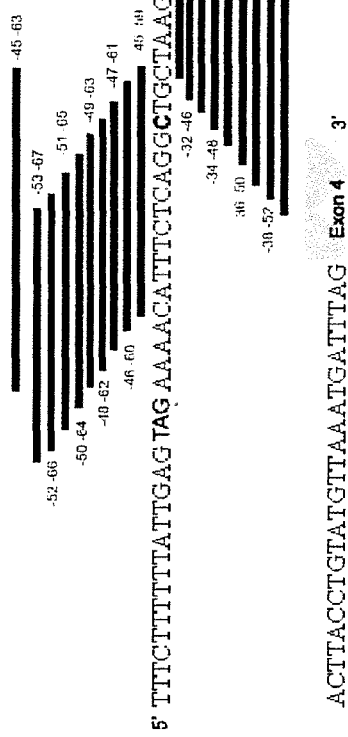
Figure 6C:
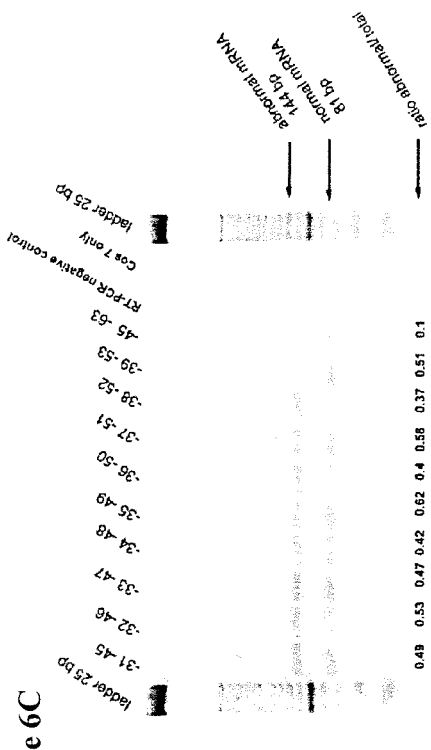
Figure 6B:
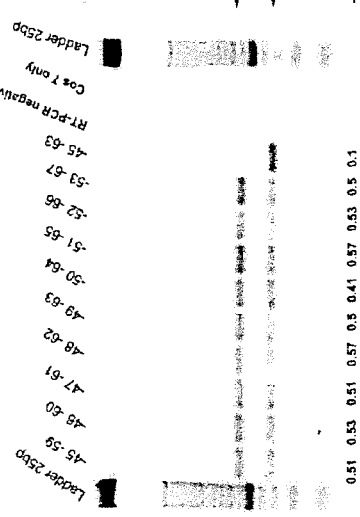

FIG. 6A-C: microwalk around position −45 in FECH intron 3

A: Schematic representation of the binding site of the 18 LNA-ASOs (SEQ ID NO: 61).

B and C: Cos 7 cells were transiently cotransfected with the FECH-C-pcDNA3 minigene, and 50, 125, or 250 nM of the appropriate LNA-ASO using lipofectamine 2000 reagent. Total RNA was extracted 24 h after transfection. RT-PCR products were analyzed on 3% agarose gel. The migration positions of the normal exon 3-4 81-bp amplimer, and the aberrantly-spliced 144-bp product are indicated on the right. Ratios of the aberrantly-spliced RNA to the total RNA are indicated at the bottom.

B: 5'microwalk from position −45.

C: 3'microwalk from position −45

FIG. 7A and B: microwalk around position −45−63

A: Schematic representation of the binding site of the 8 LNA-ASOs (SEQ ID NO: 62).

B: Cos 7 cells were transiently cotransfected with the FECH-C-pcDNA3 minigene and 50, 125, or 250 nM of the appropriate LNA-ASO using lipofectamine 2000 reagent. Total RNA was extracted 24 h after transfection. RT-PCR products were analyzed on 3% agarose gel. The migration positions of the normal exon 3-4 81-bp amplimer, and of the aberrantly-spliced 144-bp product are indicated on the right. Ratios of the aberrantly-spliced RNA to the total RNA are indicated at the bottom.

FIG. 8: WT FECH gene expression during in-vitro erythroid differentiation of $CD34^+$ cells isolated from the peripheral whole blood of a normal subject. WT FECH RNA was analyzed by RT-qPCR with specific primers of the normal exon 3-4 spliced RNA and normalized using two genes (B2M and HPRT1).

Figure 9:
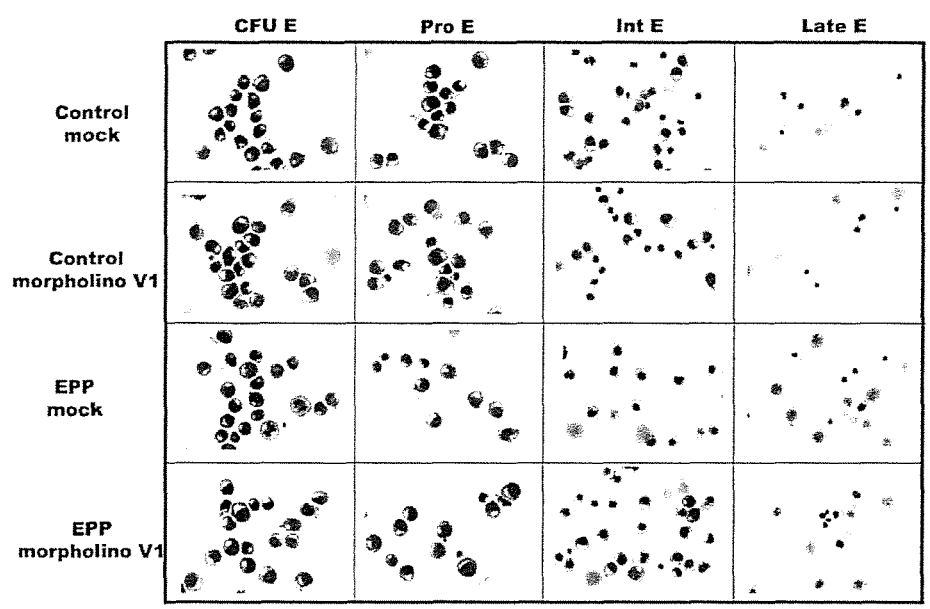

FIG. 9: Cytospin preparations of cells stained with May-Grünwald Giemsa illustrate the morphologic changes.

Four populations of erythroid cells were distinguished—corresponding to stages characterized by the predominance of CFU E, pro-erythroblasts (Pro E), basophilic and polychromatophilic stage (Int E), and reticulocytes (Late E). Representative pictures were taken at ×40 magnification. "Control": normal subject C; "EPP": overt EPP patient A.

EXAMPLE 1

Antisense Oligonucleotide-Based Therapy in Human Erythropoietic Protoporphyria

Erythropoietic Protoporphyria (EPP, MIM 177000) is a rare inherited disorder caused by the partial mitochondrial deficiency of ferrochelatase (FECH, EC 4.99.1.1.), the last enzyme in the heme biosynthesis pathway (Puy et al. 2010) (Balwani et al. 1993). FECH is an inner mitochondrial membrane enzyme that catalyzes the insertion of the ferrous iron into free protoporphyrin IX (PPIX) to form heme. FECH deficiency in bone marrow erythroid cells leads to the overproduction and accumulation of PPIX in the erythrocytes, and then to secondary accumulation of PPIX in the plasma, skin, bile and feces (Puy et al. 2010). The commonest clinical manifestation is lifelong acute photosensitivity of sun-exposed skin, first appearing in early childhood. Although it is generally a benign disease, hepatic complications such as cholelithiasis or, in about 2% of cases, cirrhosis with rapidly fatal liver disease, may occur (Bloomer et al. 1998; Meerman 2000; Lyoumi et al. 2011).

Cases of EPP have been reported in Europe, USA, China and Japan. So far, no case of EPP has been reported in Black African subjects. Previously we showed that the clinical outcome of EPP is due to the inheritance of a common hypomorphic allele in trans to a deleterious mutation; this reduces FECH activity below a critical 35% threshold of enzyme activity (Gouya et al. 1996; Gouya et al. 1999). A common intronic Single Nucleotide Polymorphism (SNP), IVS3-48C/T (rs2272783, FIG. 1A), is responsible for the low-expression of the hypomorphic IVS3-48C allele by modulating the use of a 3' constitutive cryptic acceptor splice site located at the intron 3-exon 4 boundary, which leads to the pseudoexon inclusion of a portion of intron 3 (60% inclusion with the IVS3-48 C allele versus 20% with the T allele). The aberrantly-spliced mRNA includes a premature stop codon, and is degraded by a nonsense-mediated mRNA decay mechanism (NMD) (Gouya et al. 2002). In overt cases, this low, steady-state mRNA level of the hypomorphic allele also results in FECH enzyme deficiency. The overall FECH activity falls below a critical threshold of about 35% of normal, below which PPIX accumulation and photosensitivity occur (Gouya et al. 2006; Tahara et al. 2010). Several studies in USA, Europe, and Asia have confirmed that this mechanism is generally operative in EPP (Risheg et al. 2003; Wiman et al. 2003; Saruwatari et al. 2006; Kong et al. 2008; Whatley et al. 2010; Balwani et al. 2013). In France more than 90% of EPP patients show this striking inheritance pattern.

Taken together, these findings suggest that therapeutic benefits in EPP patients might be achieved by even a modest increase in wild-type (WT) FECH protein. Thus, correcting this single splicing mutation is an attractive strategy that could improve the condition of the vast majority of EPP patients. Antisense oligonucleotides (ASOs), which are generally used to inhibit gene expression, can also be used to modulate pre-mRNA splicing by targeting splice sites, or positive or negative elements that affect splice-site selection (Kole et al. 2012).

In this study, we applied two strategies to identifying ASOs that repress the partial inclusion of intron 3 in FECH mRNA: firstly an ASO-tiling method to search for regulating cis-acting elements residing within the 130-bp stretch upstream of exon 4, and secondly an orientated strategy using three ASOs targeting the putative IVS3-48C-activated cryptic branch point, the cryptic acceptor splice site, or both the cryptic splice site and the IVS3-48C nucleotide (FIG. 1B and Table 1). For all these experiments, we used 15-mer Locked Nucleic Acids (LNAs) that demonstrate nuclease resistance, and enhance affinity for hybridization to complementary RNA (Kurreck et al. 2002). This class of ASO is highly effective for modifying pre-mRNA splicing patterns (Roberts et al. 2006). To investigate the effects of individual ASOs on splicing, we constructed two FECH minigenes (FECH-C-pcDNA3 and FECH-T-pcDNA3) comprising exon 3 (121 bp), a shortened intron 3 (300 bp, with either the IVS3-48C or the IVS3-48T genotype) and exon 4 (193 bp). They were transfected into Cos 7 cells using lipofectamine reagent (Invitrogen, Lyon, France). Two days after transfection, exon 3-4 FECH mRNA was analyzed by RT-PCR, using a pair of human primers (Supplementary table 1). These primers did not amplify the endogenous Cos 7 FECH transcript (FIG. 1C). The extent of intron-3 inclusion was calculated as the ratio between the density of the abnormally-spliced FECH mRNA to that of the normally- plus abnormally-spliced mRNA. FECH minigene transfection in Cos 7 cells recapitulated the splicing pattern as shown in lymphoblastoid cell lines (LBCL) of IVS3-48C/C or T/T patients (Gouya et al. 2002). The FECH-C-pcDNA3 minigene revealed a ratio of about 60%, and the FECH-T-pcDNA3 minigene one of 20%. For the ASO-tiling experiments, we cotransfected individually the FECH-C-pcDNA3 minigene with each of the ASOs (supplementary FIG. 1A and supplementary Table 1; 13 ASOs, overlapping by 5 nt). None of the 13 LNA-ASOs used in the initial "walk" along intron 3 reduced intron 3 retention (supplementary FIG. 1B). Only ASO −45−63, obtained using the orientated strategy, complementary to a sequence including the IVS3-48 polymorphism and the 3' cryptic acceptor splice site, reduced intron 3 inclusion to about 20% of the total RNA, a level similar to the level obtained with the FECH-T-pcDNA3 construction (FIG. 1C). A dose-response effect showed that this effect was already evident at 50 nM ASO concentration, and was maximal at 125 nM (FIG. 1C). To further refine the targeting sequence, we microwalked around the −45 position using 18 additional 15 mer LNA-ASOs (Supplementary FIG. 2A and supplementary Table 2). Again, none displayed any effect, demonstrating that both the IVS3-48 locus and the −63 acceptor splice site have to be targeted to achieve the repression of intron 3 inclusion (Supplementary FIG. 2B). Finally, we tested whether the splicing was sensitive to the length of the ASO. We used eight additional LNA-ASOs, which were one or two bases longer than LNA-ASO −45−63 at either one or both extremities (Supplementary FIG. 2A and supplementary Table 1). All these LNA-ASOs reduced intron 3 inclusion, but none was more effective than the −45−63 LNA-ASO (Supplementary FIG. 3B).

Figure 2A:
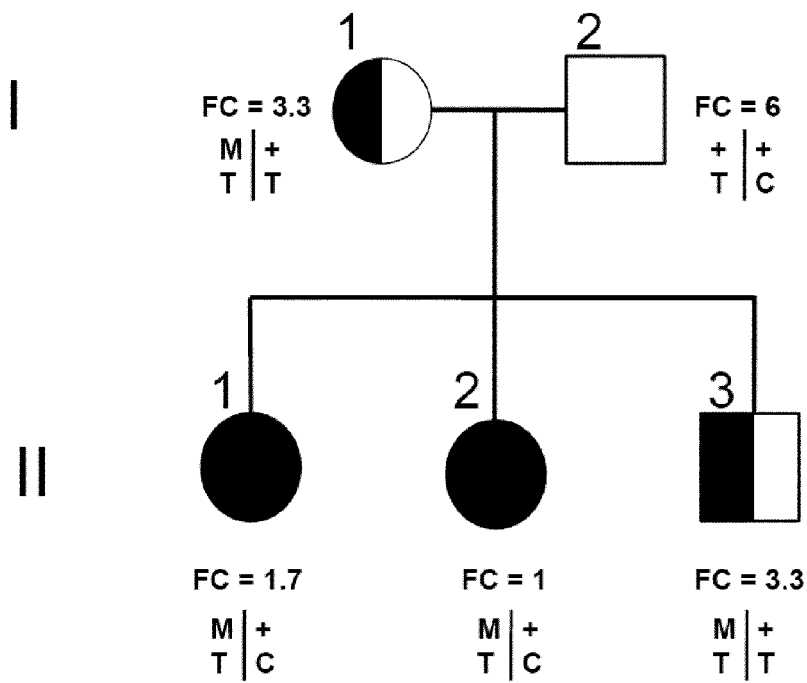
Figure 2B:
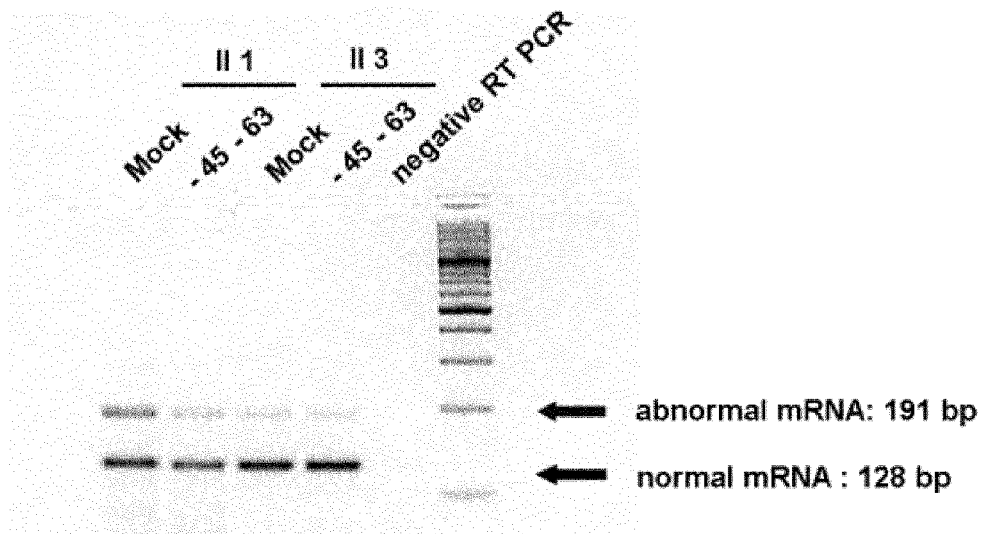
Figure 2C:
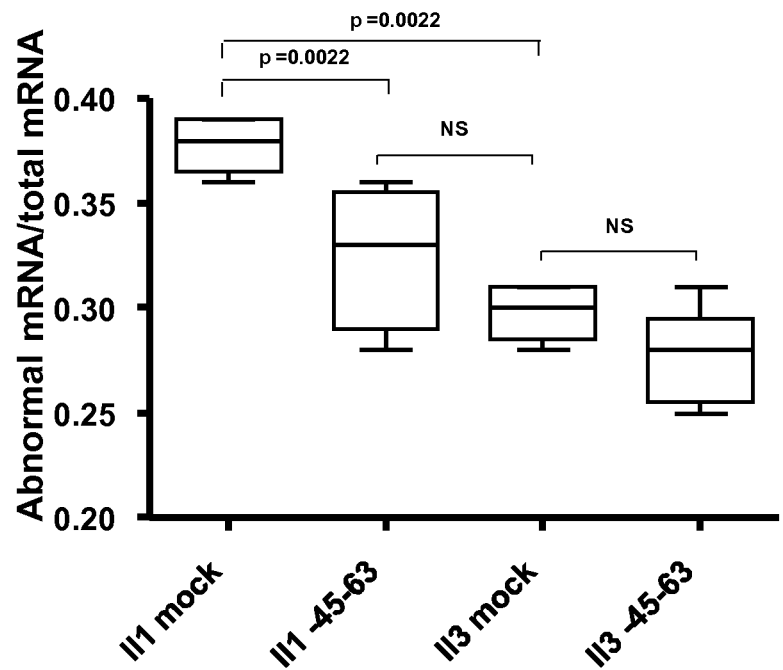
Figure 2D:
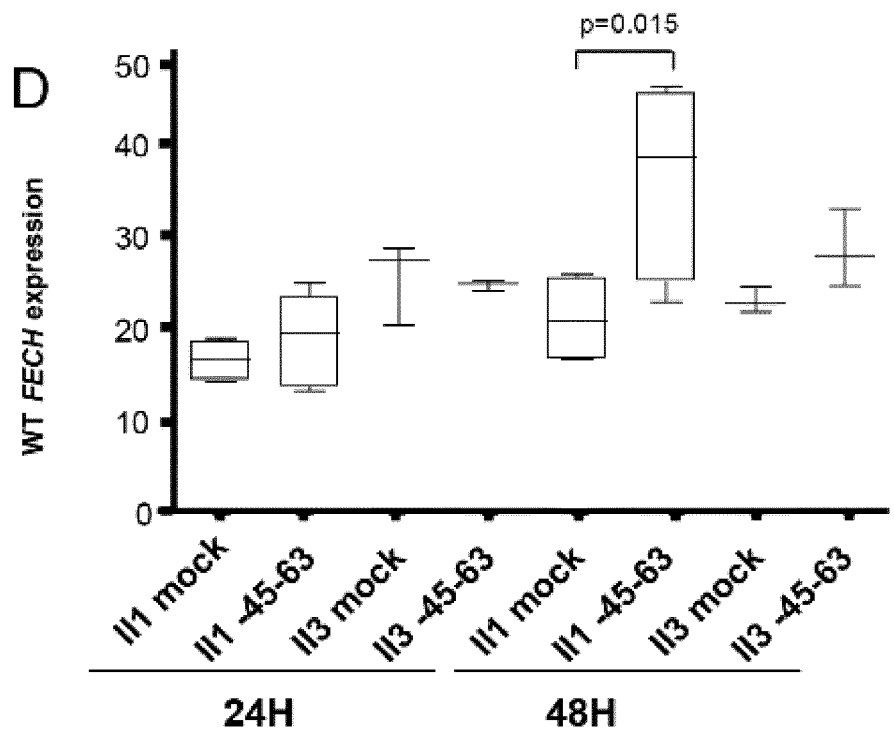

To further investigate whether by reducing intron 3 retention, we also induced a higher WT intron 3-exon 4 splicing rate, we measured splicing in the LBCL of a sib-pair of EPP patients (FIG. 2B). The FECH genotype of both patients included the c.709delT mutation, which was trans to the IVS3-48C allele in the overtly EPP patient (subject II1, showing classical symptoms of EPP), and trans to a T allele in the asymptomatic EPP patient (FIG. 2A, subject II3, without any symptoms of EPP). The optimal concentration (125 nM) of −45−63 LNA-ASO or mock-ASO (a complementary sequence of the −45−63 ASO) were transfected using lipofectamine reagent. Three hours after transfection, emetine (Sigma-Aldrich, Saint-Quentin Fallavier, France) was added to the medium to block NMD. Forty-eight hours after ASO transfection, endogenous exon 3-4 splicing was analyzed using exon 3-4 RT-PCR (Supplementary Table 1; FIG. 2B). As expected, intron 3 retention in the LBCL of patient II3 (transfected with the mock ASO) was about 25% lower than in the LBLCL of patient II1 (abnormal mRNA/ total mRNA ratio 0.30 versus 0.38, p=0.0022; FIG. 2C). Interestingly, when the LBCL of patient II1 was transfected with the −45−63 LNA-ASO, the ratio fell to a level almost identical to that measured in the asymptomatic II3 patient (0.32 versus 0.30, not significant; FIG. 2C). WT FECH mRNA was then measured by RT-qPCR using primers specific to the WT exon 3-4 boundary (Supplementary Table 1). Twenty-four hours after ASO transfection, no differences were observed between the mock and −45−63 LNA-ASO-transfected cells (FIG. 2D). As expected, WT FECH mRNA was 30% more abundant in LBCLs of the asymptomatic versus symptomatic patient. Forty-eight hours after transfection with the −45−63 LNA-ASO, LBCL of the overt II1 patient showed a considerable increase in WT FECH mRNA, which was 1.8 and 1.7 times higher than the II1 mock transfected cells and the II3 −45−63 LNA-ASO transfected cells, respectively (FIG. 2D).

In summary, we identified a −45−63 nt sequence which when targeted by ASO reduced intron 3 inclusion in LBCL with a IVS3-48T/C genotype to a level comparable to that of the IVS3-48T/T genotype, and increased WT mRNA production in the cells of an overt patient to a higher level than that measured in an asymptomatic EPP patient. Taken together, these results suggest that the −45−63 ASO has considerable therapeutic potential. The −45−63 sequence is intronic with regard to physiological exon 3-4 splicing, but becomes exonic when the 63 cryptic splice site is used. The mechanisms underlying splicing redirection from the 3-4 boundary of the cryptic to the physiological exon are complex, and not yet fully understood. Blocking exclusively either the 3' aberrant splice site (6 ASOs: −50−64; −51−65; −52−66; −53−67; −61−75 and −54−74) or the IVS3-48 locus (11 ASOs: −34−48 to −39−53; −41−65 and −45−59 to −48−62) was not sufficient to restore proper splicing. In the competition between the cryptic and the physiological splice sites, redirection of splicing toward the physiological site has to include blocking both the cryptic splice site and the IVS3-48 locus, suggesting that this region may include an exonic splicing enhancer (ESE) of cryptic splicing or an intronic splicing inhibitor (ISI) of exon 3-4 splicing.

Bone marrow erythroblasts are the primary source of excessive PPIX production in EPP; secondarily this leads to its accumulation in other tissues. This means that these cells are the relevant tissue to be targeted by a therapeutic approach. This prompted us to test the effect of the −45−63 nt ASO (referred to as V1 hereafter) on erythroid precursor cells from overt and asymptomatic EPP patients.

We cultured CD34+-derived erythroid progenitors from two overt EPP patients (patients A and B), one asymptomatic patient (patient D), and one control subject (subject C). Overt patients A and B both had the classical history of skin photosensitivity beginning during childhood, a high level of erythrocyte free protoporphyrin, and 25-30% residual FECH activity in peripheral blood mononuclear cells. Their FECH genotype consisted of a deleterious FECH mutation in trans to the hypomorphic IVS3-48C allele (Table 2). The nonsense mutation of patient A introduced a premature stop codon probably associated with mRNA degradation, and the mutation in patient B was responsible for aberrant exon 10 splicing conserving the correct reading frame. The third patient (patient D) was an asymptomatic EPP patient with a homozygous IVS3-48T/T genotype. Her erythrocyte free protoporphyrins were slightly above the normal limit (×2), and her FECH activity was about 50% below normal in peripheral blood mononuclear cells (Table 2). Her daughter is an overt EPP patient, with a classical history of cutaneous photosensitivity, a high level of free PPIX accumulation in erythrocytes (65 µmol/L RBC), a more pronounced FECH deficiency in lymphocytes than her mother (1.2 versus 1.8 for her mother), and an IVS3-48C allele inherited from the healthy father (Table 2). Our study was conducted in accordance with the World Medical Association Declaration of Helsinki ethical principles for medical research involving human subjects, and its subsequent amendments. All patients gave informed consent before undergoing investigation.

The phenotype differentiation of erythroid cells was monitored by flow cytometry (FACS Canto II, BD Biosciences, Le Pont de Claix, France). Cells were stained with fluorescently-labeled antibodies against CD34-PE (A07776, Beckman Coulter, Roissy CDG, France), CD36-FITC (IM0766U, Beckman Coulter), CD71-FITC (IM0483, Beckman Coulter), and GPA-PE (MHGLA04, Invitrogen). Hemoglobinisation was monitored daily by benzidine staining. Cell morphology was established after May-Grünwald-Giemsa staining of cytospin preparations using light microscopy.

For the oligonucleotide treatment, liposomal transfections of LNA-ASO V1 were ineffective due to their high toxicity and poor transfection efficiency (data not shown). We therefore used a free uptake method by adding a morpholino-ASO to the culture medium at a final concentration of 45 µM (Sazani et al. 2001). The original method was developed by R. Kole to direct morpholino-ASOs to erythroid precursors in order to restore human beta globin gene expression in Human IVS2-654 thalassemic erythroid cells (Suwanmanee et al. 2002). The authors also showed that adding labelled morpholinos to the culture medium from day 8 to 17 resulted in strong nuclear staining. The morpholinos were prepared and purified by Gene Tools, LLC (Philomath, USA). Two morpholino-ASOs were used, targeting the −45−63 sequence in either the antisense (PMO-V1) or the complementary sequence for the mock oligonucleotide as control (PMO-mock), respectively. The oligonucleotides were labelled using fluorescein isithiocyanate (FITC).

The effects on splicing and on PPIX overproduction were analyzed sequentially during the differentiation of the erythroid progenitors. Due to the limited number of cells available, FECH activity could not be used for these experiments. WT FECH mRNA and ALAS2 mRNA were quantified by RT-qPCR (Supplementary Table 1). Protoporphyrin overproduction was analyzed by flow cytometry (excitation at 405 nm, emission at 660 nm, Canto II, Becton Dickinson France, Rungis) at four time points during the erythroid culture, and the results were normalized by FITC fluorescence to allow for the exact amount of ASO taken in by the cells (FIG. 3).

These points were established on the basis of the expression of surface markers (CD71, GPA), corresponding to the major stages of development: CFU E (Colony unit etc. $CD71^{low}$, $GPA^-$), pro-erythroblasts (Pro E; $CD71^{high}$, $GPA^{-/low}$), intermediate (Int E; $CD71^{high}$, $GPA^{high}$) and late (Late E; $CD71^{low}$, $GPA^{high}$) erythroblasts. To determine the optimal conditions for antisense oligonucleotide treatments, a culture of CD34+ mononuclear cells isolated from whole peripheral blood from a healthy control was established. The time course of FECH mRNA expression was assayed by RT-qPCR. FECH mRNA increased dramatically from the CFU E stage to the Late E stage, with a 23 fold induction (FIG. 8). Parallel erythroid differentiation was confirmed on the basis of the cell morphology (FIG. 9), and by the progressive appearance of hemoglobinized cells ranging from 0% hemoglobinization at the CFU E stage to >95% at the Late E stage. Morpholino oligonucleotides were added before inducing heme production at the CFU E stage (after approximately 7 days in culture), and were maintained at the same concentration until mature cells were obtained.

Figure 3B:
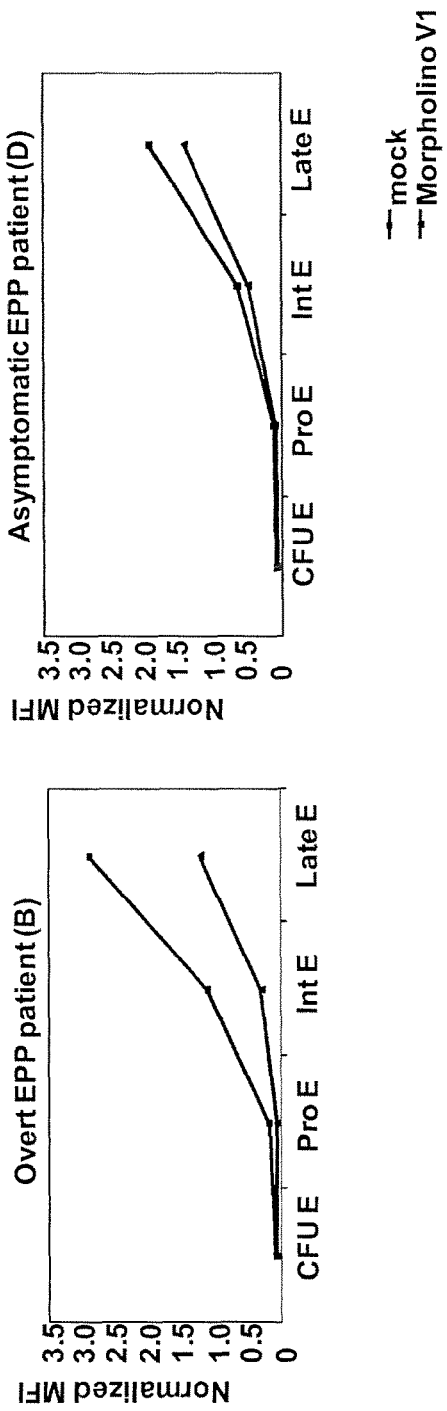

Two independent experiments were set up, one using cells from subjects A and C, and the other with those from subjects B and D (FIG. 3). WT FECH mRNA was quantified by RT-qPCR at the late E stage, when the preliminary experiment had shown that FECH mRNA expression was highest (FIG. 8). At this stage of differentiation, antisense ASO-treated cells from patients A and B showed increases of 58% and 98%, respectively, in WT FECH mRNA as compared to the mock treated cells (Table 3). In the first experiment, FECH mRNA in V1 treated cells of patient A remained 50% lower than in control subject C. This could have been due to the severity of the mutations: a one base pair deletion introducing a premature STOP codon for patient A potentially leading to a null allele. The improvement in FECH gene expression could be attributed mainly to the redirection of splicing, but could also have been achieved as a result of an overall improvement in heme biosynthesis. Indeed, the ALAS2 gene, the key regulator of erythroid heme biosynthesis, was over-expressed compared to that in the mock-treated cells at the same stage of differentiation in V1-treated cells (44% and 74% improvement for patients A and B, respectively, Table 3). PPIX accumulation was monitored during cell differentiation; in cells treated with the V1 morpholino, we observed a cumulative reduction of PPIX accumulation as erythroid differentiation progressed, culminating at the late E end point stage in a 44% reduction for patient A and a 58% reduction for patient B, versus their respective mock-treated cells (FIGS. 3A and B). Nevertheless, in overt patient A, PPIX accumulation remained higher than in the WT IVS3-48T/T control (subject C). Interestingly, PPIX accumulation decreased in overt EPP patient B to a level similar to that found in the asymptomatic patient D (FIG. 3B). This result was in agreement with the total erythrocyte PPIX measured in 40 EPP families showing that the asymptomatic EPP patients accumulated 2.5 times more PPIX than healthy subjects, even though this remained at subclinical levels (FIG. 4).

This is the first demonstration that the exon 3-4 splicing repair, not only improves WT FECH mRNA production, but also reduces PPIX accumulation in erythroid progenitors. Taken together, these results showed that the oligonucleotide-driven shift in splicing from the cryptic exon 3-4 splice site to the WT site, as demonstrated in LBCLs from EPP patients, can also occur in primary cultures of erythroid progenitors, and can increase WT FECH mRNA to such an extent that it drastically reduces the accumulation of PPIX. It is possible to speculate that this reduction in PPIX accumulation observed in erythroid cells from an overt patient could reach a level that would be sufficiently low to suppress skin sensitivity in vivo.

The correction of FECH exon 3-4 splicing is an attractive therapeutic approach for EPP, because the IVS3-48C allele is present in more than 90% of overt patients. Moreover a modest increase in FECH activity is sufficient to shift the patient's status from overt to asymptomatic. Since the correction will occur in bone marrow erythroblasts, will persist in circulating mature erythrocytes, and since the lifespan of mature erythrocytes is about 120 days, it is likely that the effects of the oligonucleotide treatment will be fairly prolonged. Most EPP patients present solely non life-threatening dermatological symptoms, and so the use of an integrative gene therapy is not currently appropriate. In contrast, antisense therapy has several advantages: i) the splicing correction occurs in the endogenous gene transcribed in its physiological environment, preventing over- or inappropriate expression; ii) a pharmalogical treatment is easier to administer than somatic gene therapy; and finally iii) this treatment can easily be simply discontinued if adverse effects occur. Targeting pre-mRNA splicing as a therapeutic strategy in Mendelian disorders was proposed several years ago for Duchenne muscular dystrophy (Wilton et al. 1999), spinal muscular atrophy (Hua et al. 2008) and β-thalassemia. In 1993, Dominski et al demonstrated that correct splicing can be restored in vitro by ASO targeting the β-globin pre-mRNA (Dominski and Kole 1993). Two laboratories were later able to improve hemoglobin synthesis in vivo, and to reduce cell damage in humanized IVS2-654 thalassemic mice using either a morpholino oligomer conjugated to a peptide, or an antisense RNA vector (Svasti et al. 2009; Xie et al. 2011). The challenge facing antisense therapeutic strategies is to develop efficient ways to target ASO to specific cells, in our case to the erythroid progenitors. For systemic administration, it is important to enhance the specificity of the treatment while reducing the concentration of ASOs so as to limit toxicity. To enhance ASO targeting, different strategies have been developed, including cell-penetrating peptides, aptamers, and cationic liposome-ASO complexes. For erythropoietic protoporphyria therapy, an interesting target could be transferrin receptor 1 (CD71), which is expressed at a very high level during the differentiation stage, when FECH incorporates iron into PPIX to form heme. Several peptides and aptamers that bind with high affinity to human or mouse CD71 and display endocytotic properties are already available (Lee et al. 2001; Wilner et al. 2012).

This proof-of-concept of the ability of the V1 antisense morpholino oligonucleotide to restore correct exon 3-4 splicing of IVS3-48 pre-mRNA associated with a major increase in WT FECH mRNA production, and finally to produce a marked reduction of PPIX accumulation in cultured erythropoietic cells from EPP patients suggests that this or similar compounds should be tested in a humanized mouse model of EPP, and possibly subsequently for treating EPP patients.

TABLE 1

LNA-ASOs used in the orientated strategy

| Position | Sequence | LNA Sequence |
|---|---|---|
| -45-63 | 5' GCAGCCTGAGAAATGTTTT 3' (SEQ ID NO: 2) | 5' gcEgcLtgEgaEatPttZt 3' |
| -54-74 | 5' GAAATGTTTTCTACTCAATAA 3' (SEQ ID NO: 11) | 5' gEaaZgtZttLtaLtcEatEa 3' |
| -97-116 | 5' AAAACATTTCTCAGGCTGC 3' (SEQ ID NO: 12) | 5' aEa aLa tZt cZc aPg cZg c 3' |

TABLE 2

FECH genotypes and phenotypes in 3 EPP patients and one control from whom the erythroid precursors were extracted.

| Patient | FECH mutation | IVS3-48 genotype | Total Erythrocyte Protoporphyrins | FECH activity | Phenotype |
|---|---|---|---|---|---|
| A | c.1038 T > G p.Y346X | C/T | 43 | 1.8 | symptomatic |
| B | c.1078-2 A > G | C/T | 45 | 1.8 | symptomatic |
| C | ND | T/T | 2.5 | 1.7 | symptomatic |
| D | WT | T/T | 1.5 | 5.6 | symptomatic |

TABLE 3

WT FECH and ALAS2 mRNA quantifications during in vitro erythropoiesis experiments.

|  |  | ALAS2 mRNA | WT FECH mRNA |
|---|---|---|---|
| Experiment 1 | | | |
| Patient A | mock | 0.25 | 0.29 |
|  | V1 | 0.36 | 0.46 |
| Control subject C | mock | 1 | 1 |
|  | V1 | 0.75 | 0.73 |
| Experiment 2 | | | |
| Patient B | mock | 0.86 | 0.96 |
|  | V1 | 1.5 | 1.9 |
| Patient D | mock | 1 | 1 |
|  | V1 | 1.14 | 0.85 |

TABLE S1

Oligonucleotides used in RT-PCR and RT-qPCR.

|  | Sense primer (5'-3') | Antisense primer (5'-3') |
|---|---|---|
| FECH Exon3-4 Cos7 cells | TGGACCGAGACCTCATGACA (SEQ ID NO: 13) | AGTCCATATCTTGATGGGGAT (SEQ ID NO: 19) |
| FECH Exon 3-4 LBLC | TAAACATGGGAGGCCCTGAAAC (SEQ ID NO: 14) | GGGTTCGGCGTTTGGCGATGAATGG (SEQ ID NO: 20) |
| WT FECH mRNA qPCR | TTCCTATTCAGAATAAGCTGGCACCAT (SEQ ID NO: 15) | GCCTCCAATCCTGCGGTACTG (SEQ ID NO: 21) |
| ALAS2 mRNA qPCR | AGGATGTGTCCGTCTGGTGTA (SEQ ID NO: 16) | TGAAACTTACTGGTGCCTGAGA (SEQ ID NO: 22) |
| B2M | TGCTGTCTCCATGTTTGATGTATCT (SEQ ID NO: 17) | TCTCTGCTCCCCACCTCTAAGT (SEQ ID NO: 23) |
| HPRT1 | TGACACTGGCAAAACAATGCA (SEQ ID NO: 18) | GGTCCTTTTCACCAGCAAGCT (SEQ ID NO: 24) |

TABLE S2

LNA-ASOs used in the intron 3 walking.
Initial walk in Intron 3

| Position | LNA sequence | Native sequence | SEQ ID NO: |
|---|---|---|---|
| -1 -15 | 5' ctEaatcEtttaEca 3' | ctaaatcatttaaca | 25 |
| -11 -25 | 5' taEcatEcaggtEag 3' | taacatacaggtaag | 26 |
| -21 -35 | 5' gtEagtPgatttZat 3' | gtaagtggattttat | 27 |
| -31 -45 | 5' ttZattLcagctZag 3' | tttattccagcttag | 28 |
| -41 -55 | 5' ctZagcEgcctgEga 3' | cttagcagcctgaga | 29 |
| -51 -65 | 5' tgEgaaEtgtttZct 3' | tgagaaatgttttct | 30 |
| -61 -75 | 5' ttZctaLtcaatEaa 3' | tttctactcaataaa | 31 |
| -71 -85 | 5' atEaaaEagaaaEaa 3' | ataaaaagaaaaaa | 32 |
| -81 -95 | 5' aaEaaaPcaaaaZtt 3' | aaaaaagcaaaattt | 33 |
| -91 -105 | 5' aaZtttaPagagLct 3' | aattttagagagcct | 34 |
| -101 -115 | 5' agLctaEcaagaZta 3' | agcctaacaagatta | 35 |
| -111 -125 | 5' gaZtaaPccttttEaa 3' | gattaagcctttaaa | 36 |
| -121 -135 | 5' ttEaaaLagaagLtt 3' | ttaaaacagaagctt | 37 |
| -45 -63 | 5' gcEgcLtgEgaEaatPttZt 3' | gcagcctgagaaatgtttt | 2 |

TABLE S2-continued

LNA-ASOs used in the intron 3 walking.
Initial walk in Intron 3

| Position | | sequence | | |
|---|---|---|---|---|
| microwalk around position -45 | | | | |
| -31 | -45 | 5' ttZattLcagctZag 3' | tttattccagcttag | 38 |
| -32 | -46 | 5' ttEttcLagcttEgc 3' | ttattccagcttagc | 39 |
| -33 | -47 | 5' taZtccEgcttaPca 3' | tattccagcttagca | 40 |
| -34 | -48 | 5' atZccaPcttagLag 3' | attccagcttagcag | 41 |
| -35 | -49 | 5' ttLcagLttagcEgc 3' | ttccagcttagcagc | 42 |
| -36 | -50 | 5' tcLagcZtagcaPcc 3' | tccagcttagcagcc | 43 |
| -37 | -51 | 5' ccEgctZagcagLct 3' | ccagcttagcagcct | 44 |
| -38 | -52 | 5' caPcttEgcagcLtg 3' | cagcttagcagcctg | 45 |
| -39 | -53 | 5' agLttaPcagccZga 3' | agcttagcagcctga | 46 |
| -45 | -59 | 5' gcEcccZgagaaEtg 3' | gcaccctgagaaatg | 47 |
| -46 | -60 | 5' caLcctPagaaaZgt 3' | caccctgagaaatgt | 48 |
| -47 | -61 | 5' acLctgEgaaatPtt 3' | accctgagaaatgtt | 49 |
| -48 | -62 | 5' ccLtgaPaaatgZtt 3' | ccctgagaaatgttt | 50 |
| -49 | -63 | 5' ccZgagEaatgtZtt 3' | cctgagaaatgtttt | 51 |
| -50 | -64 | 5' ctPagaEatgttZtc 3' | ctgagaaatgttttc | 52 |
| -51 | -65 | 5' tgEgaaEtgtttZct 3' | tgagaaatgttttct | 53 |
| -52 | -66 | 5' gaPaaaZgttttLta 3' | gagaaatgttttcta | 54 |
| -53 | -67 | 5' agEaatPttttcZac 3' | agaaatgttttctac | 55 |
| -45 | -63 | 5' gcEgcLtgEgaEatPttZt 3' | gcagcctgagaaatgtttt | 2 |
| microwalk around position -45-63 | | | | |
| -43 | -63 | 5' tagcEgcLtgEgaEatPttZt 3' | tagcagcctgagaaatgtttt | 33 |
| -44 | -63 | 5' agcEgcLtgEgaEatPttZt 3' | agcagcctgagaaatgtttt | 4 |
| -45 | -63 | 5' gcEgcLtgEgaEatPttZt 3' | gcagcctgagaaatgtttt | 2 |
| -43 | -64 | 5' tagcEgcLtgEgaEatPttZtc 3' | tagcagcctgagaaatgttttc | 5 |
| -44 | -64 | 5' agcEgcLtgEgaEatPttZtc 3' | agcagcctgagaaatgttttc | 7 |
| -45 | -64 | 5' gcEgcLtgEgaEatPttZtc 3' | tagcagcctgagaaatgtttt | 56 |
| -43 | -65 | 5' tagcEgcLtgEgaEatPttZtct 3' | agcagcctgagaaatgtttt | 57 |
| -44 | -65 | 5' agcEgcLtgEgaEatPttZtct 3' | agcagcctgagaaatgttttc | 9 |
| -45 | -65 | 5' gcEgcLtgEgaEatPttZtct 3' | gcagcctgagaaatgttttct | 10 |

For each ASO in intron 3, the position corresponds to the distance of the 5' and 3' nucleotide from the first exon 4 base. The sequences are shown on the complementary strand. LNA bases are "E" for Adenine, "P" for Guanine, "Z" for Thymine and "L" for Cytosine.

REFERENCES

Throughout this application, various references describe the state of the art to which this invention pertains. The disclosures of these references are hereby incorporated by reference into the present disclosure.

Balwani M, Bloomer J, Desnick R (1993) Erythropoietic Protoporphyria, Autosomal Recessive.

Balwani M, Doheny D, Bishop D F, Nazarenko I, Yasuda M, Dailey H A, Anderson K E, Bissell D M, Bloomer J, Bonkovsky H L, Phillips J D, Liu L, Desnick R J (2013) Loss-of-Function Ferrochelatase and Gain-of-Function Erythroid 5-Amino levulinate Synthase Mutations Causing Erythropoietic Protoporphyria and X-Linked Protoporphyria in North American Patients Reveal Novel Mutations and a High Prevalence of X-Linked Protoporphyria. Mol Med Bloomer J, Bruzzone C, Zhu L, Scarlett Y, Magness S, Brenner D (1998) Molecular defects in ferrochelatase in patients with protoporphyria requiring liver transplantation. J Clin Invest 102:107-114

Dominski Z, Kole R (1993) Restoration of correct splicing in thalassemic pre-mRNA by antisense oligonucleotides. Proc Natl Acad Sci USA 90:8673-8677

Gouya L, Deybach J C, Lamoril J, Da Silva V, Beaumont C, Grandchamp B, Nordmann Y (1996) Modulation of the phenotype in dominant erythropoietic protoporphyria by a low expression of the normal ferrochelatase allele. Am J Hum Genet 58:292-299

Gouya L, Martin-Schmitt C, Robreau A M, Austerlitz F, Da Silva V, Brun P, Simonin S, Lyoumi S, Grandchamp B, Beaumont C, Puy H, Deybach J C (2006) Contribution of a common single-nucleotide polymorphism to the genetic predisposition for erythropoietic protoporphyria. Am J Hum Genet 78:2-14

Gouya L, Puy H, Lamoril J, Da Silva V, Grandchamp B, Nordmann Y, Deybach J C (1999) Inheritance in erythropoietic protoporphyria: a common wild-type ferrochelatase allelic variant with low expression accounts for clinical manifestation. Blood 93:2105-2110

Gouya L, Puy H, Robreau A M, Bourgeois M, Lamoril J, Da Silva V, Grandchamp B, Deybach J C (2002) The penetrance of dominant erythropoietic protoporphyria is modulated by expression of wildtype FECH. Nat Genet 30:27-28

Hua Y, Vickers T A, Okunola H L, Bennett C F, Krainer A R (2008) Antisense masking of an hnRNP A1/A2 intronic splicing silencer corrects SMN2 splicing in transgenic mice. Am J Hum Genet 82:834-848

Kole R, Krainer A R, Altman S (2012) RNA therapeutics: beyond RNA interference and antisense oligonucleotides. Nat Rev Drug Discov 11:125-140

Kong X F, Ye J, Gao D Y, Gong Q M, Zhang D H, Lu Z M, Lu Y M, Zhang X X (2008) Identification of a ferrochelatase mutation in a Chinese family with erythropoietic protoporphyria. J Hepatol 48:375-379

Kurreck J, Bieber B, Jahnel R, Erdmann V A (2002) Comparative study of DNA enzymes and ribozymes against the same full-length messenger RNA of the vanilloid receptor subtype I. J Biol Chem 277:7099-7107

Lee J H, Engler J A, Collawn J F, Moore B A (2001) Receptor mediated uptake of peptides that bind the human transferrin receptor. Eur J Biochem 268:2004-2012

Lyoumi S, Abitbol M, Rainteau D, Karim Z, Bernex F, Oustric V, Millot S, Letteron P, Heming N, Guillmot L, Montagutelli X, Berdeaux G, Gouya L, Poupon R, Deybach J C, Beaumont C, Puy H (2011) Protoporphyrin retention in hepatocytes and Kupffer cells prevents sclerosing cholangitis in erythropoietic protoporphyria mouse model. Gastroenterology 141:1509-1519, 1519 e1501-1503

Meerman L (2000) Erythropoietic protoporphyria. An overview with emphasis on the liver. Scand J Gastroenterol Suppl:79-85

Puy H, Gouya L, Deybach J C (2010) Porphyrias. Lancet 375:924-937

Risheg H, Chen F P, Bloomer J R (2003) Genotypic determinants of phenotype in North American patients with erythropoietic protoporphyria. Mol Genet Metab 80:196-206

Roberts J, Palma E, Sazani P, Orum H, Cho M, Kole R (2006) Efficient and persistent splice switching by systemically delivered LNA oligonucleotides in mice. Mol Ther 14:471-475

Saruwatari H, Ueki Y, Yotsumoto S, Shimada T, Fukumaru S, Kanekura T, Kanzaki T (2006) Genetic analysis of the ferrochelatase gene in eight Japanese patients from seven families with erythropoietic protoporphyria. J Dermatol 33:603-608

Sazani P, Kang S H, Maier M A, Wei C, Dillman J, Summerton J, Manoharan M, Kole R (2001) Nuclear antisense effects of neutral, anionic and cationic oligonucleotide analogs. Nucleic Acids Res 29:3965-3974

Suwanmanee T, Sierakowska H, Fucharoen S, Kole R (2002) Repair of a splicing defect in erythroid cells from patients with beta-thalassemia/HbE disorder. Mol Ther 6:718-726

Svasti S, Suwanmanee T, Fucharoen S, Moulton H M, Nelson M H, Maeda N, Smithies O, Kole R (2009) RNA repair restores hemoglobin expression in IVS2-654 thalassemic mice. Proc Natl Acad Sci USA 106:1205-1210

Tahara T, Yamamoto M, Akagi R, Harigae H, Taketani S (2010) The low expression allele (IVS3-48C) of the ferrochelatase gene leads to low enzyme activity associated with erythropoietic protoporphyria. Int J Hematol 92:769-771

Whatley S D, Mason N G, Holme S A, Anstey A V, Elder G H, Badminton M N (2010) Molecular epidemiology of erythropoietic protoporphyria in the U.K. Br J Dermatol 162:642-646

Wilner S E, Wengerter B, Maier K, de Lourdes Borba Magalhaes M, Del Amo D S, Pai S, Opazo F, Rizzoli S O, Yan A, Levy M (2012) An RNA alternative to human transferrin: a new tool for targeting human cells. Mol Ther Nucleic Acids 1:e21

Wilton S D, Lloyd F, Carville K, Fletcher S, Honeyman K, Agrawal S, Kole R (1999) Specific removal of the nonsense mutation from the mdx dystrophin mRNA using antisense oligonucleotides. Neuromuscul Disord 9:330-338

Wiman A, Floderus Y, Harper P (2003) Novel mutations and phenotypic effect of the splice site modulator IVS3-48C in nine Swedish families with erythropoietic protoporphyria. J Hum Genet 48:70-76

Xie S Y, Li W, Ren Z R, Huang S Z, Zeng F, Zeng Y T (2011) Correction of beta654-thalassaemia mice using direct intravenous injection of siRNA and antisense RNA vectors. Int J Hematol 93:301-310

The invention claimed is:

1. A method for increasing the amount of functional FECH in an erythroid cell carrying the hypomorphic allele IVS3 48C/T (rs2272783) in trans to a deleterious mutation in the FECH gene comprising the step of bringing the erythroid cell into contact with at least one antisense oligonucleotide (ASO) consisting of the sequence as set forth by SEQ ID NO: 2 (5' gcagcctgagaaatgtttt 3') to prevent splicing of the cryptic exon inserted into the mutant IVS3 48C/T (rs2272783) FECH mRNA.

2. The method of claim 1 wherein the ASO is stabilized.

3. The method of claim 1 wherein the ASO is selected from the group consisting of oligodeoxyribonucleotides, oligoribonucleotides, Locked Nucleic Acid (LNA) oligonucleotides, morpholinos oligonucleotides, tricyclo-DNA-antisense oligonucleotides, and U7- or U1-mediated ASO or conjugate products thereof.

4. The method of claim 1 wherein the ASO is conjugated to a molecule selected from the group consisting of aptamers, polypeptides, and antibodies.

5. The method of claim 4 wherein the polypeptides and aptamers bind with high affinity to the human transferrin receptor CD71 and display endocytotic properties.

6. A method for the treatment of Erythropoietic Protoporphyria in a patient harbouring the common hypomorphic allele IVS3 48C/T (rs2272783) in trans to a deleterious mutation in the FECH gene, comprising
administering to said patient a therapeutically effective amount of at least one antisense oligonucleotide (ASO) consisting of the sequence as set forth by SEQ ID NO: 2 (5' gcagcctgagaaatgtttt 3'), in order to prevent splicing of the cryptic exon inserted into the mutant IVS3 48C/T (rs2272783) FECH mRNA and treat the Erythropoietic Protoporphyria.

7. A pharmaceutical composition comprising at least one antisense oligonucleotide (ASO) selected from the group consisting of Locked Nucleic Acid (LNA) oligonucleotides, morpholinos oligonucleotides, tricyclo-DNA-antisense oligonucleotides, and U7- or U1-mediated ASO or conjugate products thereof which consists of the sequence as set forth by SEQ ID NO: 2.

8. The method of claim 3, wherein the conjugate products are peptide-conjugated ASO or nanoparticle-complexed ASO.

9. The pharmaceutical composition of claim 7, wherein the conjugate products are peptide-conjugated ASO or nanoparticle-complexed ASO.

* * * * *

SEQUENCE LISTING

```
<160> NUMBER OF SEQ ID NOS: 62

<210> SEQ ID NO 1
<211> LENGTH: 7277
<212> TYPE: DNA
<213> ORGANISM: Homo sapiens
```

<400> SEQUENCE: 1

```
aggtcagggg gctggggacg cgcgtgggga tcgctacccg gctcggccac tgctgggcgg    60
acacctgggc gcgccgccgc gggaggagcc cggactcggg ccgaggctgc ccaggcaatg   120
cgttcactcg gcgcaaacat ggctgcggcc ctgcgcgccg cgggcgtcct gctccgcgat   180
ccgctggcat ccagcagctg gagggtctgt cagccatgga ggtggaagtc aggtgcagct   240
gcagcggccg tcaccacaga aacagcccag catgcccagg gtgcaaaacc tcaagttcaa   300
ccgcagaaga ggaagccgaa aactggaata ttaatgctaa acatgggagg ccctgaaact   360
cttggagatg ttcacgactt ccttctgaga ctcttcttgg accgagacct catgacactt   420
cctattcaga ataagctggc accattcatc gccaaacgcc gaacccccaa gattcaagag   480
cagtaccgca ggattggagg cggatccccc atcaagatat ggacttccaa gcagggagag   540
ggcatggtga agctgctgga tgaattgtcc cccaacacag cccctcacaa atactatatt   600
ggatttcggt acgtccatcc tttaacagaa gaagcaattg aagagatgga gagagatggc   660
ctagaaaggg ctattgcttt cacacagtat ccacagtaca gctgctccac cacaggcagc   720
agcttaaatg ccatttacag atactataat caagtgggac ggaagcccac gatgaagtgg   780
agcactattg acaggtggcc cacacatcac ctcctcatcc agtgctttgc agatcatatt   840
ctaaaggaac tggaccattt tccacttgag aagagaagcg aggtggtcat tctgttttct   900
gctcactcac tgcccatgtc tgtggtcaac agaggcgacc catatcctca ggaggtaagc   960
gccactgtcc aaaaagtcat ggaaaggctg gagtactgca acccctaccg actggtgtgg  1020
caatccaagg ttggtccaat gccctggttg ggtcctcaaa cagacgaatc tatcaaaggg  1080
ctttgtgaga gggggaggaa gaatatcctc ttggttccga tagcatttac cagtgaccat  1140
attgaaacgc tgtatgagct ggacatcgag tactctcaag tttttagccaa ggagtgtgga  1200
gttgaaaaca tcagaagagc tgagtctctt aatggaaatc cattgttctc taaggccctg  1260
gccgacttgg tgcattcaca catccagtca aacgagctgt gttccaagca gctgaccctg  1320
agctgtccgc tctgtgtcaa tcctgtctgc agggagacta atccttctt caccagccag  1380
cagctgtgac ccccgccggt ggaccccgtg gcgttaggca aatgcccaac ctccagatac  1440
ctccgatgtg gagagggtgt tatttagaga tcaaggaagg aagtcatcct tccttgatat  1500
atatacagcc tttgggtaca aattgtgtgg tttcttgagg attggactct tgatggattt  1560
ctattttat ataactatac agtaagcatt tgtattttct ctctctaggt ataagttact  1620
agtttggaat gtccatcagg acctttaata atgagttaa aaatttgtct tatgagacac  1680
acctatttaa gtacagattt tggctttatt gcccaaaacc ctcctgaaag ggtacggaga  1740
gtcccctctg tgggctggca gtgtaatga atctgttta gtctcgtgca tatagttgct  1800
gttttttaaa tgaacacagt tgagtatttg aagtgaattt gaaaagaaa tgttacttaa  1860
tctttcccta agcccatggg ttacagaatg ctagggaggc aatttggtta cctgcaatgg  1920
ctgcttttgc cagcgaggcc accattcatt ggtcatcttg gtatttgtgt gtgaatctca  1980
ctttcctcaa tgtaaaaagg aatcaagtat ggatttcaga ggtgctctta gattccccat  2040
acacccaagg gtaataaacg tgtacaagta cagtgttcat gatacgtgcc ttggtgggag  2100
tccgtggtgc cacagggaag gggctcccac tgcttctggt ctccagggac agtgctgctg  2160
gaaaggctag tgatgagctt caccсctggag ctcctcccgg gaccttgcaa gcctctccat  2220
ccagcatctt ctctatctta gttgaatgcc ttctttctga acatttgttt taagaattat  2280
```

```
tttataaagt caacaatact ttgcttgaat tctttcttaa tttacgattt tttattataa    2340
aaatgtatag tgatacaatg ggacatgtga agaatacaga aaagtaacca ctttaatgca    2400
ataactgtta tcataatatt gtatttcgtg gtagtccttt cctgtagata tttttaatgc    2460
catttaatgc cattgtcacc ttggatttat gagtgaaaag tgtttctaaa aatatagaaa    2520
taatgtcaga tcagagtctg atcttctatg tttgtattta aatggattaa aagatccccg    2580
gtggttccat gaagaatttg taaagatcac tttctctttc ctccaagccc tgaaactttg    2640
ttcttcaaaa gagcgtttct tttttttttt tttttagcc agtttataaa gtggaagtat    2700
taggagattc ataaatcttc tatattgaga attggctatg ttaataaata ttacaacatc    2760
attaaggttt tagctaagtt tgattcatgc tgtctgttaa atcaaaactg atctaaatca    2820
gaattattaa atgtgaggag ctttttttaat acaggaaaag aaacatgtca tccacttgag    2880
ttaatagttt tcctacgttg atgacagccc tcatgagtag catccacatt tttaaaattt    2940
caaattggtt tttctactag tagattgtgt ttctagagaa agatacaagg cataggtgat    3000
tgtttaggat tttcctctag cctttgccat taccttttttg gggatgaggt tcacagtaga    3060
ctttgagtga ccgtcccacc gtgaagtgaa ttctctgagc tggtggtgtg gtgctggaag    3120
gaaggttatt tttggagcca ctctctcccc ttaaggatat ttcccaaggg cctgcttcaa    3180
ttctttgatg actttagagg tgaaaaaata tttttatgga gatgatgcag aaaactccaa    3240
ttcaggagcc cttgcgagta tatctgaagc acttatttgc taaggaaacc tgaattgata    3300
gcagtactgt gctgtctgga ataatgtcct tgatactgag ttgggaccag actggctttt    3360
atagtgacag gcaaagagga aatttattgag atcactgctc atggcatttg ttgctgtaag    3420
aagtgttgcc tttgattgtt actaaccacg gatgggtaac ggtcatacat taggctagtg    3480
tttggtagga caaaatcttt ttagagcttt gagaattgtc atcctgttgg tcaactttga    3540
aatacaaatg tttgccctgg taattagcaa tgaactgctg gcagtttctt cagctgtgta    3600
tatacggatc tggcttttaa ttgatgaatc aacttctaca gaaacttttg cagggacagt    3660
gttgatgagg cagtttagct tgccagggtg atgataaagc ccaggtccct gcatgtatag    3720
tgctcttcta aagaatatgc attcttgaac tacttaactt tttaaaaatc acaataaatt    3780
tttgcactca aaatttgctt cgtatcagga gaaatgaact cattgttttg ttttgttttt    3840
tttttttttt aagatggagt cttgctatgt cacccaggct ggagggcagt ggtgcgatct    3900
cggctcactg ctacttccac ctcctgggct caagtgatcc tcccacctca gcctccaagt    3960
agctgggact acaggagtgc ttcaccacgc tgggctactt ttttatattt tttgtagaga    4020 tgggttttttg ccatgttgtc caggctggtc ttgaactcct gggctcaagg gattctcctg    4080
cctcagtctc ccaaagtgct gggattacaa ggatgagcct ctgcacctgg ccctgaactc    4140
attattaaaa gccctttaaa tgtgaggctg ggtgccgtgc cttacatgtg taattccaat    4200
actttggaag gccaaggttg gaggattgct tgatcccaag agttcaagac cagcctgggc    4260 aacatagggga gaccctgact ctacaaaaaa taaagtaaaa attaactggg tgtagtgtca    4320
catgcctgta gttccagcta cttaggaggc tgaggtggta ggattgcttg agcccagcag    4380
tttgaggttg cagtgaggtg tgattgcacc actgcactcc agcctgggtg acagaggaag    4440
accctgtccc aaaaccaaaa aaaagaaaag aaatacagag actgggtcat ttacaaagga    4500
aagaggttta attgactcgg ttcggctttc tgaggaagcc ttaggaaatt gacaatcatg    4560
gcagaagggg aagcagatgt cttacatggc agtgagtgag agcaagcaaa ggggaagagc    4620 cccctattataa aaccatcaga tctcgtgaga actggctgtc acaagaacag catggggaa    4680
```

```
ctgtctccat gttccaatct ccttccacca ggtccctccc tcaacacgtg gggattatgg    4740
ggattacaat ttgaaatgag atttgggtgg ggaacagagc caaatcatat cattccaccc    4800
tggcccctcc caaatcacat gtccttttta catttcaaaa ccaatcatgc cttcacaaca    4860
gtcctccaga gtcttaactc attccagcat taacccaaaa gtccaagttc aaagtctcat    4920
ccaagacaag gcaagtccct tctgcctgtg agcctgtaac attaaaagca agttagtgac    4980
ttccaagata caatgggagt acagacattg gtaaatgttc ccattccaaa tgggagaaat    5040
tggccaaaac acagggcta caggcccat gcaccactgc actccactgt gcaagtctga    5100
aacccggcag ggcactcctt aaattttttt tttttttttt tgagatggag tctcgctctg    5160
ttgcccaagc tggagtacag tggcacgatc tcggctcact gcaacctccg cctcttgggt    5220
tcaaaggatc atcctgcctc agcctccgga gtagctgggc tactcaggcg tgtgccacca    5280
tgcccggcta atttttgtat ttttagtaga gatggggcct gaccatgttg gtcaggctgg    5340
tctctaattc ctgacctcgt gatccacccg cctcagcctc tgaaagtgtt gggattacag    5400
gcgtgagcca ccatccccgg cctactcaat aaatcttaaa gttccggaat aatctccttt    5460
gactccatgt ctcacctcca ggtcacgctg atgcaagagg tgggctaatc tttctagtaa    5520
attccatatt taattcaaga aaccataact taaggcatgt aaaagagatc ctttgctcaa    5580
tgtgatgcca ttgtgcttat ccaaagtata ttattattac ccacaagggg tgagagatta    5640
ggctgcagcc ataccccaag tggagtgagc agcaagacct gcccctgct cagagtgtag    5700 atgactgggg gcacctgcat tcctaggggc tctgccgtat gagctcctgt cgatgcggca    5760
aaggaccacc ttgcccaacg acagcgggaa ggcagaattt aaagctggca gctgtaagcg    5820
aacgtctatg tgtgcgcacg ggggcacgtg aaggcacagg tgcatcagcc aagaacctcc    5880
aattcacctc ttaaccttct cacctcacct gaaacccctt ctgccagaat cctgaaggtg    5940
gcccaggaac agggctccta acgttaggtg gaaatgggaa attcattgag atgtcacaag    6000
ctggaataag aaaattctga gctcacccgg aaactaatgc cctaaattaa gattattcag    6060
cttctcaatt tttaatagca aaatggagac ctgagtgtgg ataactttta gtatctgtgg    6120
gggatcctgg aaccaattcc ctgccaatat agaaggacaa ctgtctacag tacttgaagt    6180
attattaact acattcgcca tgctgtatgt tagatcccca gaacatattt atcctgcata    6240
tctaaaattt tgatcatttt acaaactttc tatttttttt gtcaatttc tccagctaga    6300 cacttgtgca atacggctat tatctgatct ttgccttaaa tgttgtgctt cttttccata    6360
tgcacgtatt ttgcaaaata taagtgtgt agagctatat agcactcagc caagtggtgg    6420
gtacctgcag gtgcttcaga gaagtaaatt gatgctgcta atatttgttg aatggcacga    6480
atatgatgag caatagcagg tggtgccctt cagccagacc atcgctccgt gcgtctgatg    6540
catcttgcca agagtagtt ctgggaggtg gttgcctcta gagaacacat tcctcctatt    6600 ctgggggtccc gtgagagaaa gaaatgcttt tgcttttgat gtgggactct tactaagcct    6660
ttcttcagag aaaaggaagt gaaaaatgca ccccatgata atcagtttct tacaacatac    6720
tgtgatagta ccggcttcgt tgttttttagc tggaatcatt agcttccatt tttagaataa    6780
cagctattgg ctaaattagg ctacagtagg ccattaagat ggatgttgga attaaaaaca    6840
tttttggaaa aaagcctgct ttgagccttt gttataagcc cttgggtaga gatctgggtc    6900
ctgtttctga tttcttgtga gccttcactc tgacagtttt gtttccagaa acacactctt    6960
agcctgctcc tgaaatggga acagacaggc caacttcccc tctccagtct cccctgcggg    7020
```

```
tcaaagcttt actttcctgt catgttaaga aagaatagat ttaaccttga taatccatgt    7080
agtattctgt atttttacct tttccttatc tgaaaaaaag tgtatatatg gcatggaatt    7140
gattgcacag gcacatggca tgttggcttg tgaaccaatt gttaaaattt caagttaatc    7200
attaaaataa tatctttcaa attaagttat attaaaaaca aaggtaacat tctaaattca    7260
aaaaaaaaaa aaaaaa                                                    7277
```

<210> SEQ ID NO 2
<211> LENGTH: 19
<212> TYPE: DNA
<213> ORGANISM: Artificial
<220> FEATURE:
<223> OTHER INFORMATION: Synthetic antisense oligonucleotide

<400> SEQUENCE: 2
gcagcctgag aaatgtttt                                                 19

<210> SEQ ID NO 3
<211> LENGTH: 21
<212> TYPE: DNA
<213> ORGANISM: Artificial
<220> FEATURE:
<223> OTHER INFORMATION: Synthetic antisense oligonucleotide

<400> SEQUENCE: 3
tagcagcctg agaaatgttt t                                              21

<210> SEQ ID NO 4
<211> LENGTH: 20
<212> TYPE: DNA
<213> ORGANISM: Artificial
<220> FEATURE:
<223> OTHER INFORMATION: Synthetic antisense oligonucleotide

<400> SEQUENCE: 4
agcagcctga gaaatgtttt                                                20

<210> SEQ ID NO 5
<211> LENGTH: 23
<212> TYPE: DNA
<213> ORGANISM: Artificial
<220> FEATURE:
<223> OTHER INFORMATION: Synthetic antisense oligonucleotide

<400> SEQUENCE: 5
tagcagcctg agaaatgttt tct                                            23

<210> SEQ ID NO 6
<211> LENGTH: 20
<212> TYPE: DNA
<213> ORGANISM: Artificial
<220> FEATURE:
<223> OTHER INFORMATION: Synthetic antisense oligonucleotide

<400> SEQUENCE: 6
gcagcctgag aaatgttttc                                                20

<210> SEQ ID NO 7
<211> LENGTH: 21
<212> TYPE: DNA
<213> ORGANISM: Artificial
<220> FEATURE:
<223> OTHER INFORMATION: Synthetic antisense oligonucleotide

<400> SEQUENCE: 7
agcagcctga gaaatgtttt c                                                21

<210> SEQ ID NO 8
<211> LENGTH: 22
<212> TYPE: DNA
<213> ORGANISM: Artificial
<220> FEATURE:
<223> OTHER INFORMATION: Synthetic antisense oligonucleotide

<400> SEQUENCE: 8
agcagcctga gaaatgtttt ct                                               22

<210> SEQ ID NO 9
<211> LENGTH: 22
<212> TYPE: DNA
<213> ORGANISM: Artificial
<220> FEATURE:
<223> OTHER INFORMATION: Synthetic antisense oligonucleotide

<400> SEQUENCE: 9
tagcagcctg agaaatgttt tc                                               22

<210> SEQ ID NO 10
<211> LENGTH: 21
<212> TYPE: DNA
<213> ORGANISM: Artificial
<220> FEATURE:
<223> OTHER INFORMATION: Synthetic antisense oligonucleotide

<400> SEQUENCE: 10
gcagcctgag aaatgttttc t                                                21

<210> SEQ ID NO 11
<211> LENGTH: 21
<212> TYPE: DNA
<213> ORGANISM: Artificial
<220> FEATURE:
<223> OTHER INFORMATION: Synthetic antisense oligonucleotide

<400> SEQUENCE: 11
gaaatgtttt ctactcaata a                                                21

<210> SEQ ID NO 12
<211> LENGTH: 19
<212> TYPE: DNA
<213> ORGANISM: Artificial
<220> FEATURE:
<223> OTHER INFORMATION: Synthetic antisense oligonucleotide

<400> SEQUENCE: 12
aaaacatttc tcaggctgc                                                   19

<210> SEQ ID NO 13
<211> LENGTH: 20
<212> TYPE: DNA
<213> ORGANISM: Artificial
<220> FEATURE:
<223> OTHER INFORMATION: Synthetic sense primer

<400> SEQUENCE: 13
tggaccgaga cctcatgaca                                                  20

<210> SEQ ID NO 14
<211> LENGTH: 22
<212> TYPE: DNA

```
<213> ORGANISM: Artificial
<220> FEATURE:
<223> OTHER INFORMATION: Synthetic sense primer

<400> SEQUENCE: 14
taaacatggg aggccctgaa ac                                             22

<210> SEQ ID NO 15
<211> LENGTH: 27
<212> TYPE: DNA
<213> ORGANISM: Artificial
<220> FEATURE:
<223> OTHER INFORMATION: Synthetic sense primer

<400> SEQUENCE: 15
ttcctattca gaataagctg gcaccat                                        27

<210> SEQ ID NO 16
<211> LENGTH: 21
<212> TYPE: DNA
<213> ORGANISM: Artificial
<220> FEATURE:
<223> OTHER INFORMATION: Synthetic sense primer

<400> SEQUENCE: 16
aggatgtgtc cgtctggtgt a                                              21

<210> SEQ ID NO 17
<211> LENGTH: 25
<212> TYPE: DNA
<213> ORGANISM: Artificial
<220> FEATURE:
<223> OTHER INFORMATION: Synthetic sense primer

<400> SEQUENCE: 17
tgctgtctcc atgtttgatg tatct                                          25

<210> SEQ ID NO 18
<211> LENGTH: 21
<212> TYPE: DNA
<213> ORGANISM: Artificial
<220> FEATURE:
<223> OTHER INFORMATION: Synthetic sense primer

<400> SEQUENCE: 18
tgacactggc aaaacaatgc a                                              21

<210> SEQ ID NO 19
<211> LENGTH: 22
<212> TYPE: DNA
<213> ORGANISM: Artificial
<220> FEATURE:
<223> OTHER INFORMATION: Synthetic sense primer

<400> SEQUENCE: 19
agtccatatc ttgatggggg at                                             22

<210> SEQ ID NO 20
<211> LENGTH: 25
<212> TYPE: DNA
<213> ORGANISM: Artificial
<220> FEATURE:
<223> OTHER INFORMATION: Synthetic sense primer

<400> SEQUENCE: 20
gggttcggcg tttggcgatg aatgg                                          25
```

<210> SEQ ID NO 21
<211> LENGTH: 21
<212> TYPE: DNA
<213> ORGANISM: Artificial
<220> FEATURE:
<223> OTHER INFORMATION: Synthetic sense primer

<400> SEQUENCE: 21
gcctccaatc ctgcggtact g                                              21

<210> SEQ ID NO 22
<211> LENGTH: 22
<212> TYPE: DNA
<213> ORGANISM: Artificial
<220> FEATURE:
<223> OTHER INFORMATION: Synthetic sense primer

<400> SEQUENCE: 22
tgaaacttac tggtgcctga ga                                             22

<210> SEQ ID NO 23
<211> LENGTH: 22
<212> TYPE: DNA
<213> ORGANISM: Artificial
<220> FEATURE:
<223> OTHER INFORMATION: Synthetic sense primer

<400> SEQUENCE: 23
tctctgctcc ccacctctaa gt                                             22

<210> SEQ ID NO 24
<211> LENGTH: 21
<212> TYPE: DNA
<213> ORGANISM: Artificial
<220> FEATURE:
<223> OTHER INFORMATION: Synthetic sense primer

<400> SEQUENCE: 24
ggtccttttc accagcaagc t                                              21

<210> SEQ ID NO 25
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 25
ctaaatcatt taaca                                                     15

<210> SEQ ID NO 26
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 26
taacatacag gtaag                                                     15

<210> SEQ ID NO 27
<211> LENGTH: 15
<212> TYPE: DNA
<213> ORGANISM: Artificial
<220> FEATURE:

<223> OTHER INFORMATION: Synthetic antisense oligonucleotide

<400> SEQUENCE: 27
gtaagtggat tttat                                                    15

<210> SEQ ID NO 28
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 28
tttattccag cttag                                                    15

<210> SEQ ID NO 29
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 29
cttagcagcc tgaga                                                    15

<210> SEQ ID NO 30
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 30
tgagaaatgt tttct                                                    15

<210> SEQ ID NO 31
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 31
tttctactca ataaa                                                    15

<210> SEQ ID NO 32
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 32
ataaaaaaga aaaaa                                                    15

<210> SEQ ID NO 33
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 33
aaaaaagcaa aattt                                                    15

```
<210> SEQ ID NO 34
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 34
aattttagag agcct                                                         15

<210> SEQ ID NO 35
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 35
agcctaacaa gatta                                                         15

<210> SEQ ID NO 36
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 36
gattaagcct ttaaa                                                         15

<210> SEQ ID NO 37
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 37
ttaaaacaga agctt                                                         15

<210> SEQ ID NO 38
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 38
tttattccag cttag                                                         15

<210> SEQ ID NO 39
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 39
ttattccagc ttagc                                                         15

<210> SEQ ID NO 40
<211> LENGTH: 15
<212> TYPE: DNA
<213> ORGANISM: Artificial
<220> FEATURE:
<223> OTHER INFORMATION: Synthetic antisense oligonucleotide
```

```
<400> SEQUENCE: 40
tattccagct tagca                                              15

<210> SEQ ID NO 41
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 41
attccagctt agcag                                              15

<210> SEQ ID NO 42
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 42
ttccagctta gcagc                                              15

<210> SEQ ID NO 43
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 43
tccagcttag cagcc                                              15

<210> SEQ ID NO 44
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 44
ccagcttagc agcct                                              15

<210> SEQ ID NO 45
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 45
cagcttagca gcctg                                              15

<210> SEQ ID NO 46
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 46
agcttagcag cctga                                              15

<210> SEQ ID NO 47
<211> LENGTH: 15
```

-continued

```
<212> TYPE: DNA
<213> ORGANISM: Artificial
<220> FEATURE:
<223> OTHER INFORMATION: Synthetic antisense oligonucleotide

<400> SEQUENCE: 47
gcaccctgag aaatg                                                   15

<210> SEQ ID NO 48
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 48
caccctgaga aatgt                                                   15

<210> SEQ ID NO 49
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 49
accctgagaa atgtt                                                   15

<210> SEQ ID NO 50
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 50
ccctgagaaa tgttt                                                   15

<210> SEQ ID NO 51
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 51
cctgagaaat gtttt                                                   15

<210> SEQ ID NO 52
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 52
ctgagaaatg ttttc                                                   15

<210> SEQ ID NO 53
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 53
```

```
tgagaaatgt tttct                                                      15

<210> SEQ ID NO 54
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 54
gagaaatgtt ttcta                                                      15

<210> SEQ ID NO 55
<211> LENGTH: 15
<212> TYPE: DNA
<213> ORGANISM: Artificial
<220> FEATURE:
<223> OTHER INFORMATION: Synthetic antisense oligonucleotide

<400> SEQUENCE: 55
agaaatgttt tctac                                                      15

<210> SEQ ID NO 56
<211> LENGTH: 21
<212> TYPE: DNA
<213> ORGANISM: Artificial
<220> FEATURE:
<223> OTHER INFORMATION: Synthetic antisense oligonucleotide

<400> SEQUENCE: 56
tagcagcctg agaaatgttt t                                               21

<210> SEQ ID NO 57
<211> LENGTH: 20
<212> TYPE: DNA
<213> ORGANISM: Artificial
<220> FEATURE:
<223> OTHER INFORMATION: Synthetic antisense oligonucleotide

<400> SEQUENCE: 57
agcagcctga gaaatgtttt                                                 20

<210> SEQ ID NO 58
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 58
tttttttctt ttttattgag tagaaaacat ttctcaggtt gctaa                     45

<210> SEQ ID NO 59
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 59
tttaaaggct taatcttgtt aggctctcta aaatttgct tttttctttt tttattgagt      60
agaaaacatt tctcaggctg ctaa                                            84

<210> SEQ ID NO 60
<211> LENGTH: 135
```

```
<212> TYPE: DNA
<213> ORGANISM: Artificial Sequence
<220> FEATURE:
<223> OTHER INFORMATION: Synthetic oligonucleotide

<400> SEQUENCE: 60
aagcttctgt tttaaaggct taatcttgtt aggctctcta aaattttgct ttttttcttt    60
tttattgagt agaaaacatt tctcaggctg ctaagctgga ataaaatcca cttacctgta   120
tgttaaatga tttag                                                    135

<210> SEQ ID NO 61
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 61
tttctttttt attgagtaga aaacatttct caggctgcta agctggaata aaatccactt    60
acctgtatgt taaatgattt ag                                             82

<210> SEQ ID NO 62
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 62 tttcttttttt attgagtaga aaacatttct caggctgcta agctggaata aaatccactt   60
acctgtatgt taaatgattt ag                                             82
```